(12) United States Patent
Prasad et al.

(10) Patent No.: US 11,344,600 B2
(45) Date of Patent: May 31, 2022

(54) STRUCTURE OF GII.4 NOROVIRUS PROTEASE—DESIGN OF BROAD-SPECTRUM PROTEASE INHIBITORS

(71) Applicant: Baylor College of Medicine, Houston, TX (US)

(72) Inventors: B. Venkataram Prasad, Houston, TX (US); Mary K. Estes, Houston, TX (US); Yongcheng Song, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 16/335,349

(22) PCT Filed: Oct. 5, 2017

(86) PCT No.: PCT/US2017/055387
§ 371 (c)(1),
(2) Date: Mar. 21, 2019

(87) PCT Pub. No.: WO2018/067847
PCT Pub. Date: Apr. 12, 2018

(65) Prior Publication Data
US 2019/0275101 A1    Sep. 12, 2019

Related U.S. Application Data

(60) Provisional application No. 62/404,332, filed on Oct. 5, 2016.

(51) Int. Cl.
| | | |
|---|---|---|
| *A61K 38/06* | (2006.01) |
| *A61K 31/27* | (2006.01) |
| *A61K 31/40* | (2006.01) |
| *A61K 31/407* | (2006.01) |
| *A61K 38/00* | (2006.01) |
| *A61K 45/06* | (2006.01) |
| *A61P 31/14* | (2006.01) |
| *G16C 20/50* | (2019.01) |
| *G16B 15/30* | (2019.01) |
| *A01N 47/12* | (2006.01) |
| *C07K 5/068* | (2006.01) |
| *C07K 5/062* | (2006.01) |
| *C07D 295/10* | (2006.01) |
| *A01N 47/28* | (2006.01) |
| *A01N 47/34* | (2006.01) |
| *C07C 201/00* | (2006.01) |
| *C07C 271/18* | (2006.01) |
| *C07D 498/08* | (2006.01) |
| *A61K 9/00* | (2006.01) |
| *A01N 43/90* | (2006.01) |
| *C07C 271/22* | (2006.01) |
| *A61K 31/395* | (2006.01) |
| *A01N 43/64* | (2006.01) |
| *A01N 37/46* | (2006.01) |

(52) U.S. Cl.
CPC .............. *A61K 38/06* (2013.01); *A01N 37/46* (2013.01); *A01N 43/64* (2013.01); *A01N 43/90* (2013.01); *A01N 47/12* (2013.01); *A01N 47/28* (2013.01); *A01N 47/34* (2013.01); *A61K 9/0014* (2013.01); *A61K 31/27* (2013.01); *A61K 31/395* (2013.01); *A61K 31/40* (2013.01); *A61K 31/407* (2013.01); *A61K 38/00* (2013.01); *A61K 45/06* (2013.01); *A61P 31/14* (2018.01); *C07C 201/00* (2013.01); *C07C 271/18* (2013.01); *C07C 271/22* (2013.01); *C07D 295/10* (2013.01); *C07D 498/08* (2013.01); *C07K 5/06017* (2013.01); *C07K 5/06026* (2013.01); *C07K 5/06052* (2013.01); *C07K 5/06086* (2013.01); *G16B 15/30* (2019.02); *G16C 20/50* (2019.02)

(58) Field of Classification Search
None
See application file for complete search history.

(56) References Cited

U.S. PATENT DOCUMENTS

| | | | | |
|---|---|---|---|---|
| 2009/0018213 A1* | 1/2009 | Snyder | ...................... | A61L 2/18 514/724 |
| 2010/0041748 A1* | 2/2010 | Milne | ..................... | C07C 69/86 514/478 |
| 2011/0183914 A1 | 7/2011 | Osborne | | |
| 2014/0243341 A1* | 8/2014 | Chang | ................ | A61K 31/5377 514/237.2 |

FOREIGN PATENT DOCUMENTS

WO    2013/166319 A1    11/2013

OTHER PUBLICATIONS

Deng et al. (Med. Chem. Commun., 2013, 4, 1354) (Year: 2013).*

(Continued)

*Primary Examiner* — Sergio Coffa
(74) *Attorney, Agent, or Firm* — Norton Rose Fulbright US LLP

(57) ABSTRACT

The present disclosure concerns inhibitors of Norovirus protease that are suitable for use against any genotype of Norovirus, including at least GII.4 Norovirus proteases. In particular embodiments, specific compositions are encompassed, including their use for prevention or treatment of Norovirus infection in an individual.

7 Claims, 32 Drawing Sheets
Specification includes a Sequence Listing.

(56) References Cited

OTHER PUBLICATIONS

Damalanka et al. "Oxadiazole-Based Cell Permeable Macrocyclic Transition State Inhibitors of Norovirus 3CL Protease", Journal of Medicinal Chemistry, vol. 59, No. 5, Jan. 29, 2016 (Jan. 29, 2016), pp. 1899-1913.
Deng et al., "Synthesis, activity and structure-activity relationship of noroviral protease inhibitors", MEDCHEMCOMM, vol. 4, No. 10, Sep. 3, 2013 (Sep. 3, 2013), p. 1354.
Hussey et al., "A Structural Study of Norovirus 3C Protease Specificity: Binding of a Designed Active Site-Directed Peptide Inhibitor", BIOCHEMISTRY, vol. 50, No. 2, Jan. 18, 2011 (Jan. 18, 2011), pp. 240-249.
Mandadapu et al., "Potent inhibition of norovirus 3CL protease by peptidyl-ketoamides and -ketoheterocycles", Bioorganic & Medicinal Chemistry Letters, vol. 22, No. 14, May 11, 2012 (May 11, 2012), pp. 4820-4826, Pergamon, Amsterdam, NL.
Weerawarna et al., "Structure-based design and synthesis of triazole-based macrocyclic inhibitors of norovirus protease: Structural, biochemical, spectroscopic, and antiviral studies", European Journal of Medicinal Chemistry, vol. 119, Apr. 25, 2016 (Apr. 25, 2016), pp. 300-318, Elsevier, Amsterdam, NL.

\* cited by examiner

FIG. 2A
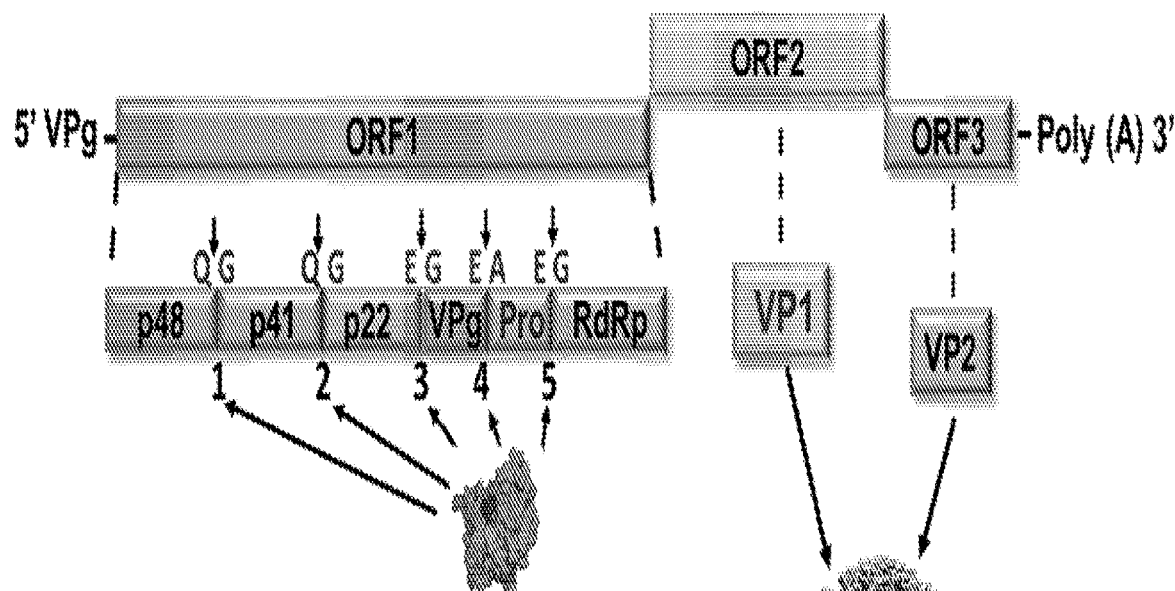
FIG. 2B
FIG. 2C
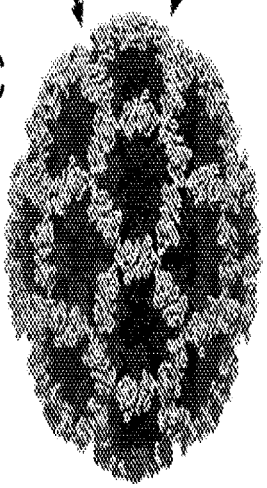
Prasad et al. Science 1999

1076

1084

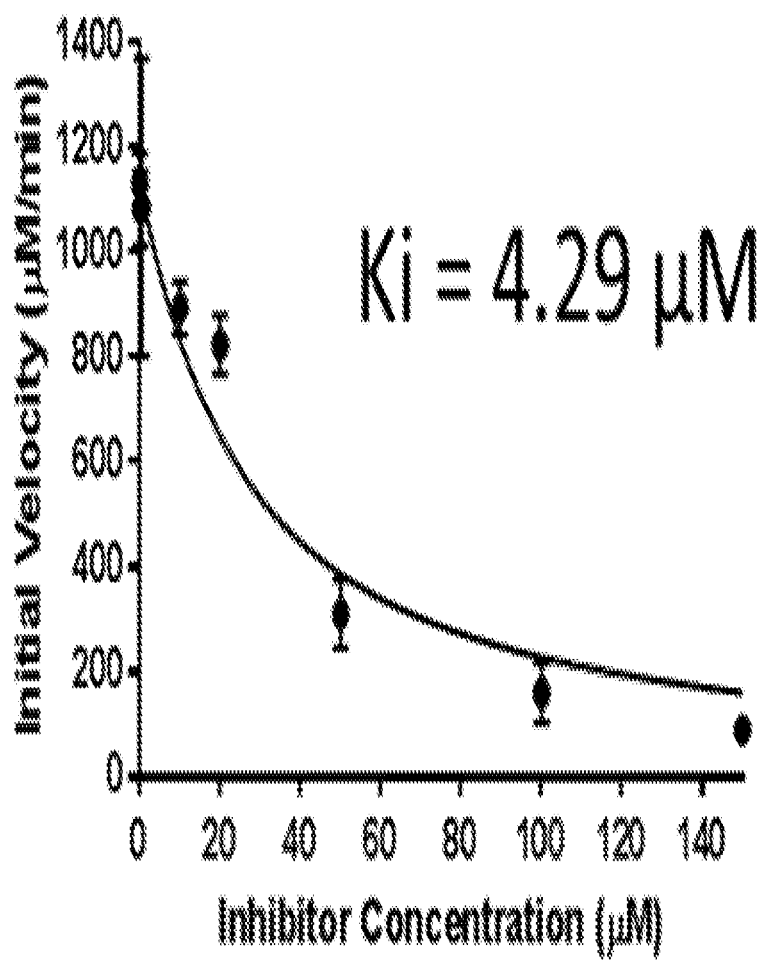
FIG. 5I NV Pro

Adapted from Muhaxhiri et al. J. Virol. 2013

FIG. 7

```
APPSIWSRIVNFGSGWGFWVSPSLFITSTHVIPQGAKEFFGVPIKQIQVHKSGFFCRLRF
APPTLWSRVTKFGSGWGFWVSPTVFITTTHVVPTGVKEFFGEPLSSIAIHQAGEFTQFRF
***..***.  .************..***.***.* *.***** *.. * .*..*** ..**

PKPIRTDVTGMILEEGAPEGTVVTLLIKRSTGELMPLAARMGTHATMKIQGRTVGGQMGM
SKKMRPDLTGMVLEEGCPEGTVCSVLIKRDSGELLPLAVRMGAIASMRIQGRLVHGQSGM
 * .* *.***.****.*****  ..****  .***.*** ***.  *.*.**** * ** **

LLTGSNAKSMDLGTTPGDCGCPYIYKRGNDYVVIGVHTAAARGGNTVICATQGSEGEATL
LLTGANAKGMDLGTIPGDCGAPYVHKRGNDWVVCGVHAAATKSGNTVVCAVQAGEGETAL
****.*** *****.***** **..******.** ***.**.,. ****.** * ***..*
```

GI.1 (NV) protease
GII.4 (HOV) protease
Syc-10 inhibitor

NV Pro
CV Pro
HOV Pro

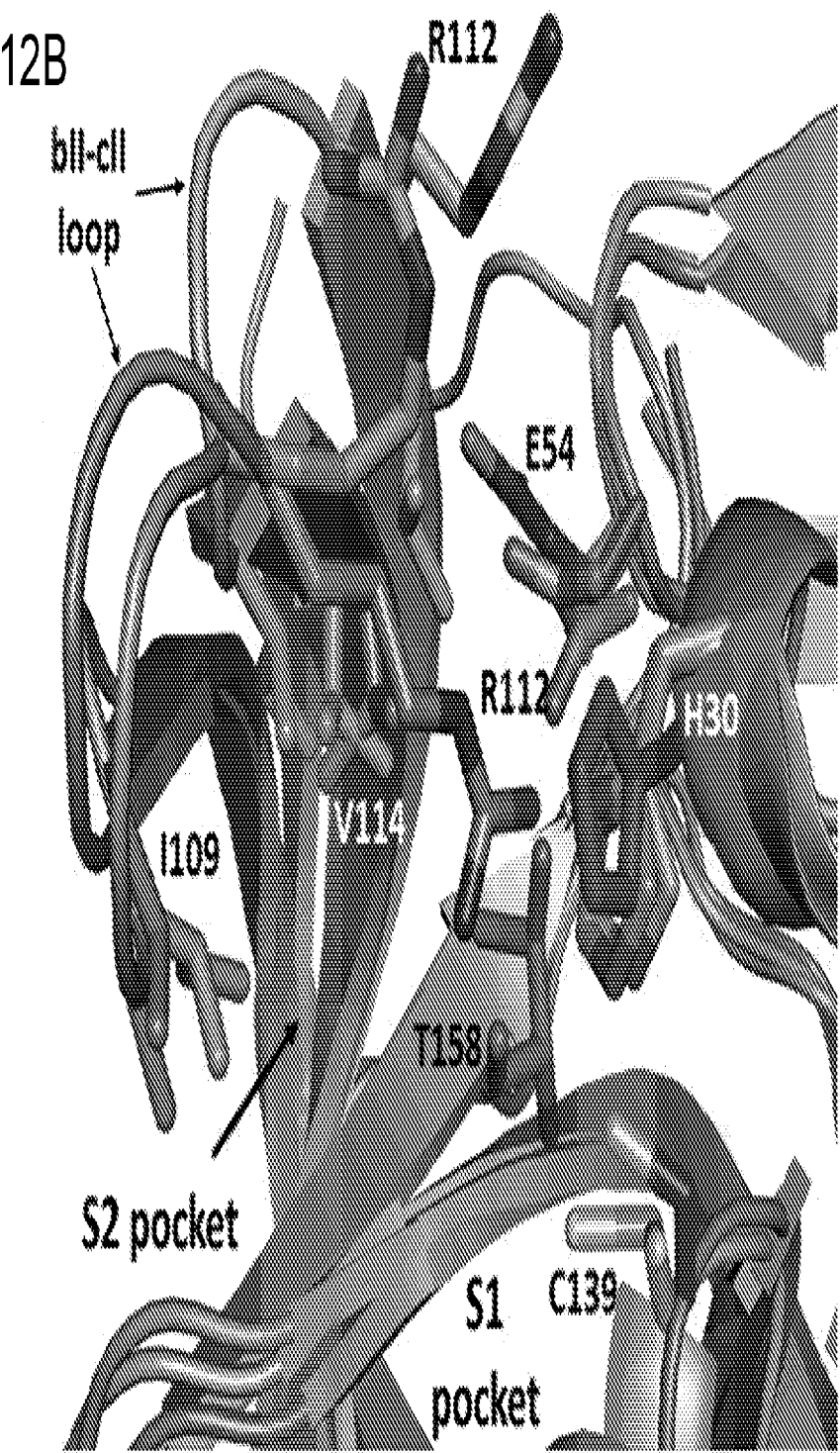

FIG. 14

| Parameter | HOV Pro |
|---|---|
| Wavelength resolution range (Å) | 39.79–2.60 (2.74–2.60) |
| Space group | $P2_12_12_1$ |
| Unit cell (Å/°) | 56.68, 91.16, 141.46/90, 90, 90 |
| No. of reflections | 99270 |
| Multiplicity | 4.3 (4.4) |
| Completeness (%) | 99.1 (99.8) |
| Mean I/sigma(I) | 17.6 (1.9) |
| Wilson B factor (Å$^2$) | 68.95 |
| R-merge (%) | 0.049 (0.841) |
| R-work (%) | 0.2257 |
| R-free (%) | 0.2664 |
| | |
| No. of atoms | |
|   Protein | 4779 |
|   Ligands | 104 |
|   Water | 28 |
| | |
| RMS bonds (Å) | 0.002 |
| RMS angles (°) | 0.505 |
| Ramachandran favored (%) | 94.7 |
| B factors (Å$^2$) | |
|   Protein | 78.24 |
|   Ligands | 89.36 |
|   Water | 79.59 |

*Values in the parenthesis are for the highest-resolution shell.

FIG. 15

| Protease, pH | $K_m$ (µM) | $K_{cat}$ ($1 \times 10^{-3} s^{-1}$) | $K_{cat}/K_m$ ($M^{-1} s^{-1}$) |
|---|---|---|---|
| HOV Pro, pH 8 | 126.8 | 106.3 | 843.7 |
| HOV Pro, pH 6.5 | — | — | — |
| HOV Pro, pH 5 | — | — | — |
| NV Pro, pH 8 | 87.9 | 125.1 | 1423.2 |
| NV Pro, pH 6.5 | 63.1 | 5.1 | 80.8 |
| NV Pro, pH 5 | — | — | — |
| HOV Pro R112A, pH 8 | 53.8 | 65.3 | 1215 |
| HOV Pro R112A, pH 6.5 | 212.5 | 4.3 | 20.2 |
| HOV Pro R112A, pH 5 | — | — | — |

FIG. 16A
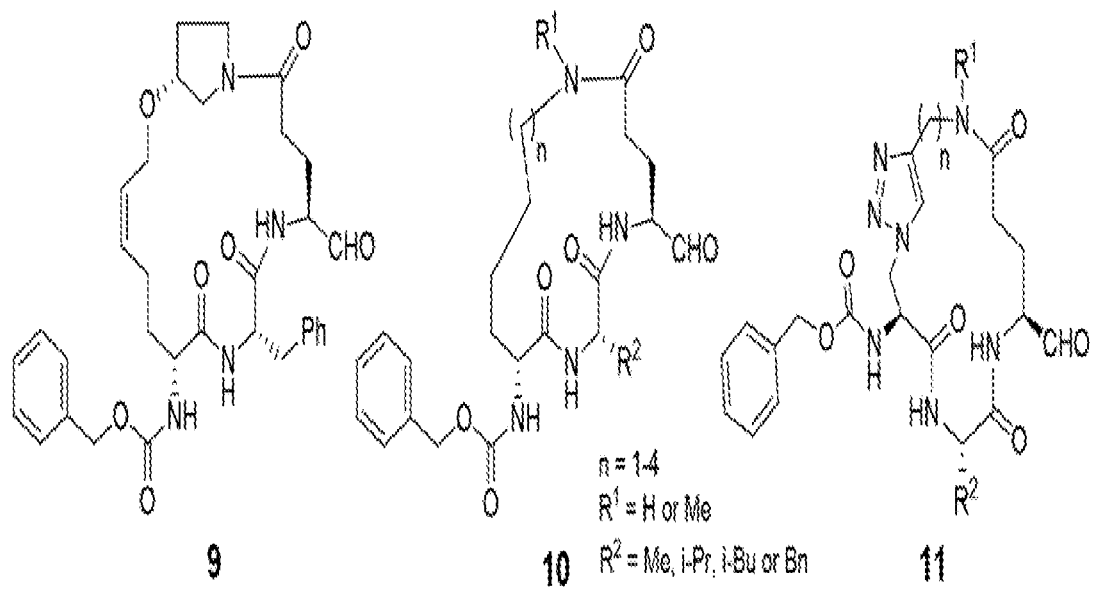
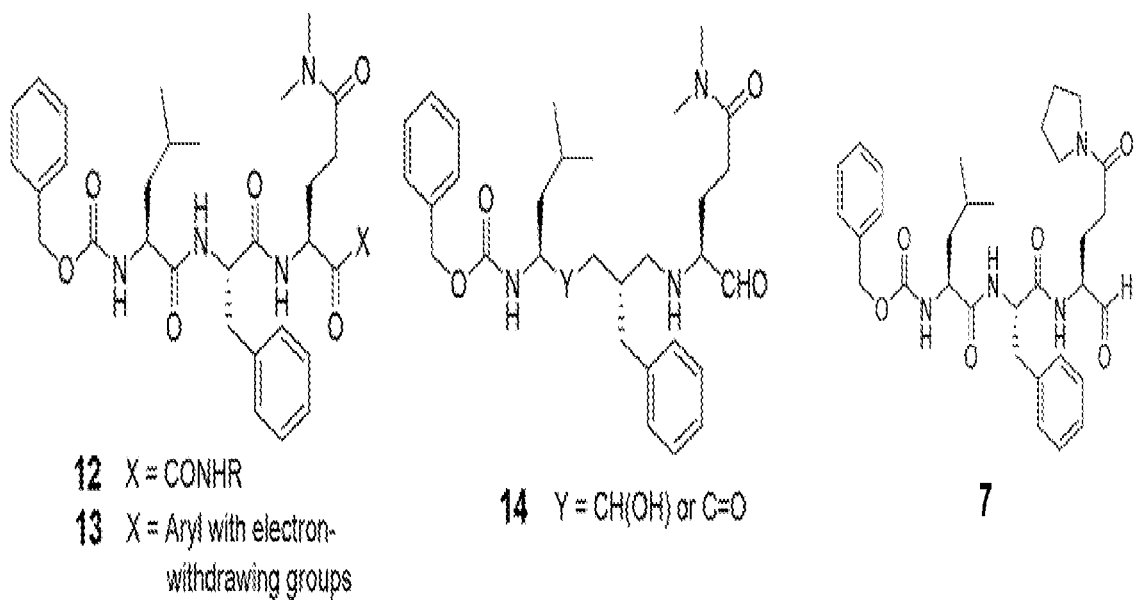

FIG. 17
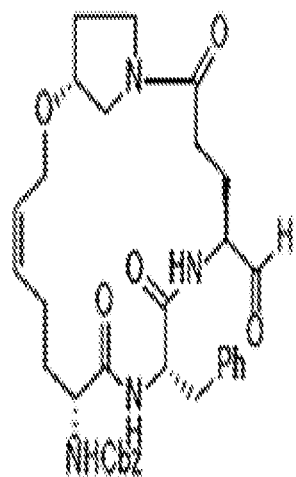
SYC-796
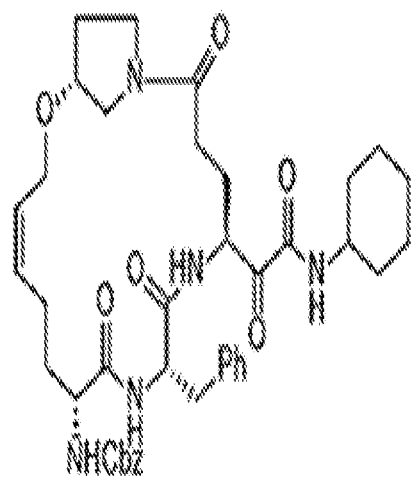
SYC-815
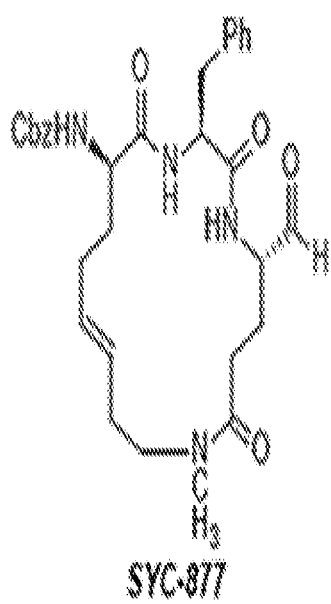
SYC-877
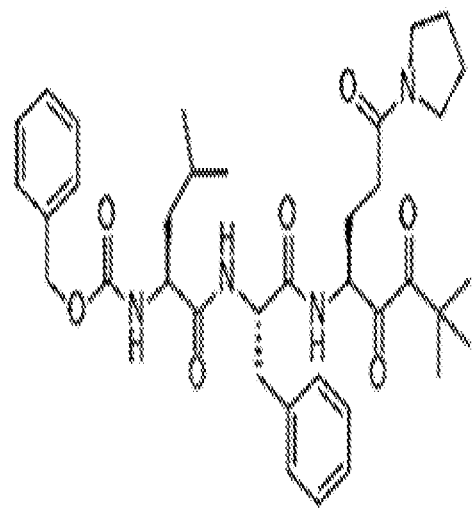
SYC-1010

FIG. 18
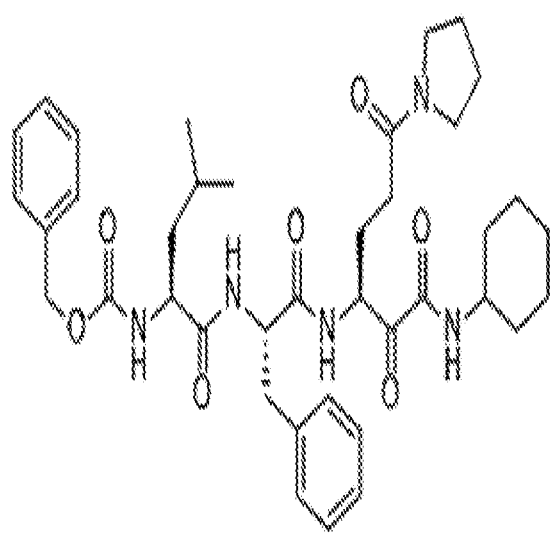
SYC-1011
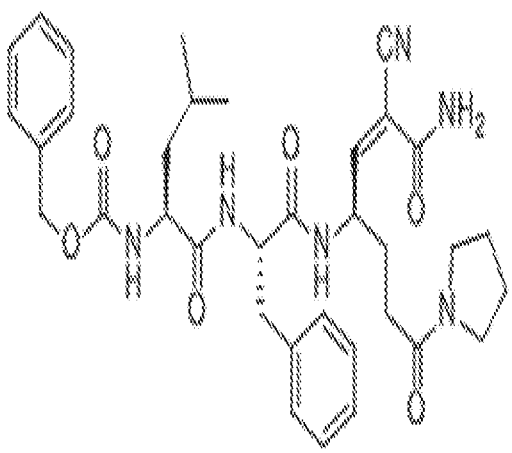
SYC-1073
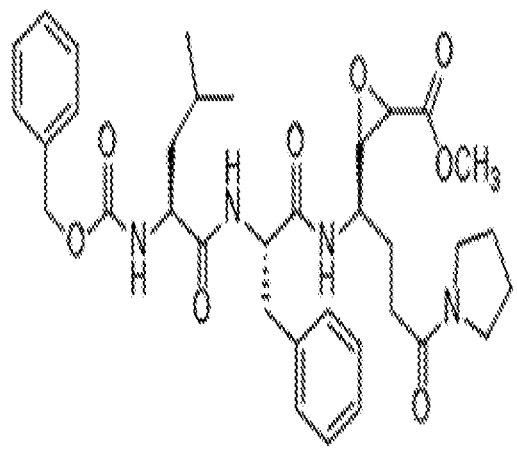
SYC-1074
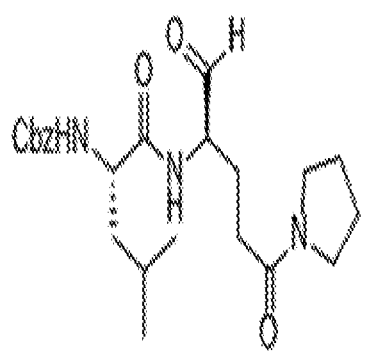
SYC-1075

FIG. 19
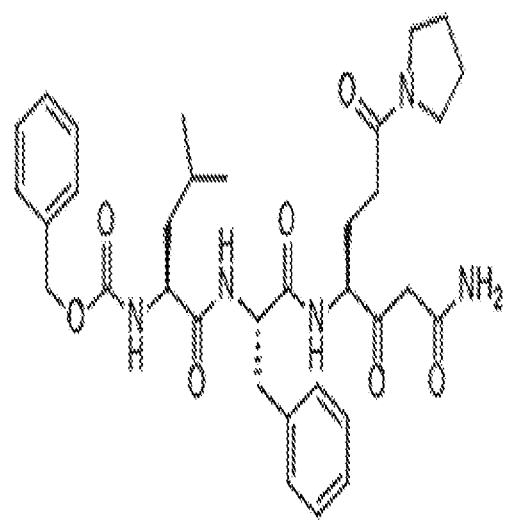
SYC-1076
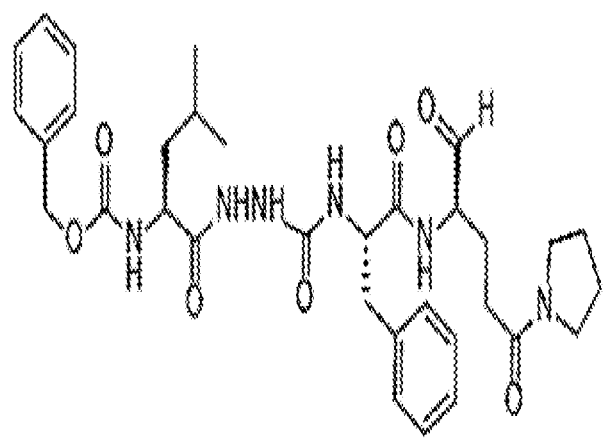
SYC-1084
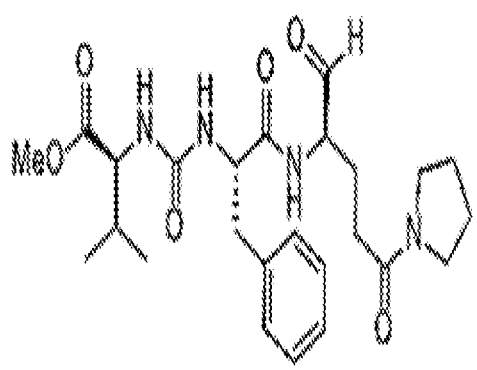
SYC-1085
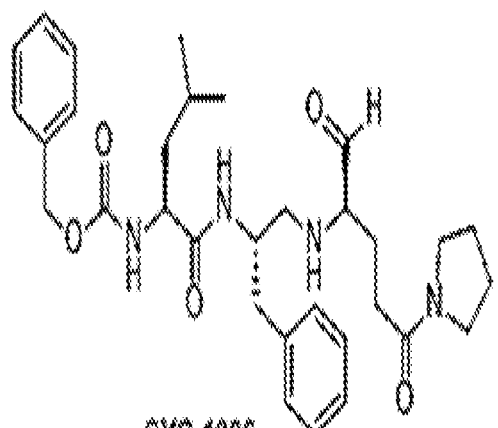
SYC-1086

SEQUENCE LISTING

```
<160> NUMBER OF SEQ ID NOS: 2

<210> SEQ ID NO 1
<211> LENGTH: 181
<212> TYPE: PRT
<213> ORGANISM: Unknown
<220> FEATURE:
<223> OTHER INFORMATION: Norwalk virus

<400> SEQUENCE: 1

Ala Pro Pro Thr Leu Trp Ser Arg Val Thr Lys Phe Gly Ser Gly Trp
1               5                   10                  15

Gly Phe Trp Val Ser Pro Thr Val Phe Ile Thr Thr Thr His Val Val
                20                  25                  30

Pro Thr Gly Val Lys Glu Phe Phe Gly Glu Pro Leu Ser Ser Ile Ala
            35                  40                  45

Ile His Gln Ala Gly Glu Phe Thr Gln Phe Arg Phe Ser Lys Lys Met
        50                  55                  60

Arg Pro Asp Leu Thr Gly Met Val Leu Glu Glu Gly Cys Pro Glu Gly
65                  70                  75                  80

Thr Val Cys Ser Val Leu Ile Lys Arg Asp Ser Gly Glu Leu Leu Pro
                85                  90                  95

Leu Ala Val Arg Met Gly Ala Ile Ala Ser Met Arg Ile Gln Gly Arg
            100                 105                 110

Leu Val His Gly Gln Ser Gly Met Leu Leu Thr Gly Ala Asn Ala Lys
        115                 120                 125

Gly Met Asp Leu Gly Thr Ile Pro Gly Asp Cys Gly Ala Pro Tyr Val
    130                 135                 140

His Lys Arg Gly Asn Asp Trp Val Val Cys Gly Val His Ala Ala Ala
145                 150                 155                 160

Thr Lys Ser Gly Asn Thr Val Val Cys Ala Val Gln Ala Gly Glu Gly
                165                 170                 175

Glu Thr Ala Leu Glu
            180

<210> SEQ ID NO 2
<211> LENGTH: 181
<212> TYPE: PRT
<213> ORGANISM: Unknown
<220> FEATURE:
<223> OTHER INFORMATION: HOV GII.4 protease

<400> SEQUENCE: 2
```

```
Ala Pro Pro Ser Ile Trp Ser Arg Ile Val Asn Phe Gly Ser Gly Trp
1               5                   10                  15
Gly Phe Trp Val Ser Pro Ser Leu Phe Ile Thr Ser Thr His Val Ile
            20              25                  30
Pro Gln Gly Ala Lys Glu Phe Phe Gly Val Pro Ile Lys Gln Ile Gln
        35              40                  45
Val His Lys Ser Gly Glu Phe Cys Arg Leu Arg Phe Pro Lys Pro Ile
    50              55                  60
Arg Thr Asp Val Thr Gly Met Ile Leu Glu Glu Gly Ala Pro Glu Gly
65              70              75                      80
Thr Val Val Thr Leu Leu Ile Lys Arg Ser Thr Gly Glu Leu Met Pro
            85                  90                  95
Leu Ala Ala Arg Met Gly Thr His Ala Thr Met Lys Ile Gln Gly Arg
            100             105             110
Thr Val Gly Gly Gln Met Gly Met Leu Leu Thr Gly Ser Asn Ala Lys
        115             120             125
Ser Met Asp Leu Gly Thr Thr Pro Gly Asp Cys Gly Cys Pro Tyr Ile
    130             135             140
Tyr Lys Arg Gly Asn Asp Tyr Val Val Ile Gly Val His Thr Ala Ala
145             150             155             160
Ala Arg Gly Gly Asn Thr Val Ile Cys Ala Thr Gln Gly Ser Glu Gly
            165             170             175
Glu Ala Thr Leu Glu
            180
```

STRUCTURE OF GII.4 NOROVIRUS PROTEASE—DESIGN OF BROAD-SPECTRUM PROTEASE INHIBITORS

CROSS-REFERENCE TO RELATED APPLICATIONS

This application is a national phase application under 35 U.S.C. § 371 that claims priority to International Application No. PCT/US2017/055387 filed Oct. 5, 2017, which claims priority to U.S. Provisional Patent Application Ser. No. 62/404,332, filed Oct. 5, 2016, all of which is incorporated herein by reference herein in their entirety.

STATEMENT REGARDING FEDERALLY SPONSORED RESEARCH OR DEVELOPMENT

This invention was made with government support under P01 AI057788 awarded by the NIH. The government has certain rights in the invention.

TECHNICAL FIELD

The technical field of the disclosure includes at least the field of molecular biology, cell biology, virology, and medicine.

BACKGROUND

Human noroviruses (NoV) are the main cause of viral gastroenteritis worldwide (Ahmed, et al., 2014; Green, et al., 2000). They are responsible for 95% of non-bacterial and 50% of all gastroenteritis outbreaks worldwide (Atmar, et al., 2006). NoVs belong to the Caliciviridae family and are divided into seven genogroups (GI-GVII), with each genogroup further divided into several genotypes. Human pathogens are restricted to genogroups GI, GII, and GIV with genogroup II and genotype 4 (GII.4) being the most prevalent, accounting for 80% of norovirus infections worldwide (Vinje, 2014; Ramani, et al., 2014; Lindesmith, et al., 2011). Both genetic and antigenic diversity of NoVs contribute to challenges in the development of effective treatments and though much needed, there are no licensed vaccines or antiviral drugs available for human NoV infections.

The NoV genome is composed of the positive-sense, single-stranded RNA with three open reading frames (ORFs) that encode a nonstructural precursor polyprotein (ORF1), a major capsid protein VP1 (ORF2), and a minor capsid protein VP2 (ORF3) (Hardy, et al., 1996; Glass, et al., 2000; Jianh, et al., 1993; Vongpunsawad, et al., 2013). The precursor polyprotein in cleaved into six nonstructural proteins by the viral protease, which is encoded by ORF1 as part of the polyprotein. NoV protease is a typical cysteine protease similar to cornavirus 3C protease and its cleavage of the polyprotein is an essential first step in viral replication and maturation (Bazan, et al., 1988; Boniotti, et al., 1994; Belliot, et al., 2003; Blakeney, et al., 2003; Hardy, et al., 2002; Someya, et al., 2005; Sosnovtsev, et al., 2002). The NoV protease, due to its role in viral replication and relatively high homology among different genogroups, is an attractive target for the development of broadly cross-reactive antivirals. To date, NoV protease structures have only been determined for the GI genogroup, with structures available for the prototype GI.1 Norwalk virus (NV Pro) and GI.4 Chiba virus (CV Pro). Crystal structures of human rhinovirus (Matthews, et al., 1994), enterovirus 71 (Wang, et al., 2011), poliovirus (Mosimann, et al., 1997), Caliciviridae member rabbit hemorrhagic disease virus (Boniotti, et al., 1994) and other viral 3C proteases revealed a common catalytic triad in the active sites with a cysteine acting as a nucleophile, histidine as a base, and glutamate or aspartate as an anion. In the NV Pro, cysteine 139 (C139), histidine 30 (H30), and glutamate 54 (E54) form a catalytic triad (Zeitler, et al., 2006; Nakamura, et al., 2005). In contrast, similar to hepatitis A virus 3C protease, the CV Pro active site functions as a catalytic dyad requiring only the C139 and H30, but not E54 for activity (Nakamura, et al., 2005; Bergmann, et al., 1997; Someya, et al., 2002). Overlay of the two structures shows further differences in the active site as well as the substrate binding pockets flanking the active site, suggesting that there may be structural variability between proteases belonging to different NoV genotypes. This variability observed in the NoV proteases may be a stumbling block in the development of effective cross-reactive inhibitors. Several groups are engaged in developing structure-based NoV protease inhibitors as a potential therapeutic against NoVs (Muhaxhiri, et al., 2013; Deng, et al., 2013; Damalanka, et al., 2017). However, the inhibitors designed thus far are based on the available NV Pro structures and though they show potent activity against GI proteases, they are not efficient in inhibiting the GII proteases for which there is no structural information available (Deng, et al., 2013). Thus, to develop a broadly cross-reactive inhibitor it is useful to determine the protease structure from members of the GII NoVs.

The present disclosure provides solutions to long-felt needs in the art to protect against or treat Noroviral infection of a variety of genogroups and genotypes.

BRIEF SUMMARY

The present disclosure is directed to methods and compositions related to protection from and/or treatment of Norovirus infection in a mammal, including a human, dog, cat, and so forth. In particular embodiments, the disclosure concerns particular compounds that are effective against any genogroup or genotype (see FIG. 1). In specific embodiments, the compositions are effective at least against GII.4 Norovirus, although other noroviruses may also be targeted by methods and compositions of the disclosure.

Embodiments of the disclosure provide a composition of matter, comprising a compound 1076 or a compound 1084 as in FIG. 5; any compound of any one of FIGS. 16-19; a compound of Formula I, II, III, IV, or V; a functionally active derivative thereof; or a mixture thereof. In specific embodiments, the disclosure encompasses a pharmaceutical composition, comprising one or more compositions that are a compound 1076 or a compound 1084 as in FIG. 5; any compound of any one of FIGS. 16-19; a compound of Formula I, II, III, IV, or V; a functionally active derivative thereof; or a mixture thereof. The pharmaceutical composition may be formulated in a cream, solution, pill, tablet, suppository, film, or enema.

In certain embodiments, provided herein is a cleaning composition, comprising one or more compositions that are a compound 1076 or a compound 1084 as in FIG. 5; any compound of any one of FIGS. 16-19; a compound of Formula I, II, III, IV, or V; a functionally active derivative thereof; or a mixture thereof. The cleaning composition may be a solution or cream. The cleaning composition may be in and/or on a substrate, such as a towel, wipe, or sponge.

In one embodiment, provided herein is a method of inhibiting a Norovirus protease, comprising the step of exposing an effective amount of one or more compositions of the disclosure to the protease. In some cases, the method occurs in vivo in an individual. In certain aspects, the individual is suspected of being infected with Norovirus, is known to be infected with Norovirus, is seropositive for Norovirus, or is at risk for being infected with Norovirus. The individual may be provided an effective amount of an additional antiviral therapy. In particular aspects, the individual is a human. In certain embodiments, the exposing step occurs on a surface and may occur in an environment prone to Norovirus infection, for example a confined environment. A confined environment may be a passenger vessel, school, arena, military environment, health care facility, food service setting, child care center, prison, recreational water setting, shopping center, or lodging facility.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 2A, 2B, and 2C illustrate the NoV genome organization. 2A. ORF1 (blue) encodes a polyprotein cleaved into six nonstructural proteins: p48, p41, p22, VPg, protease and RNA dependent RNA polymerase. The five dipeptide cleavage sites in the polyprotein are shown with black arrows indicating the cleavage site and the respective amino acids that flank the sites. 2B. Cleavage sites (P1/P1') for the GI.1 virus with neighboring amino acid residues recognized by the viral protease during proteolytic processing of the polyprotein. GII.4 residue differences are shown in parentheses. 2C. VP1 is the major capsid protein and is encoded by ORF2. VP2 is encoded by ORF3 and is a minor structural protein. Both VP1 and VP2 form the viral capsid. Shown is the X-ray structure of the recombinant virus like particle (VLP).

FIG. 7 shows sequence alignment of the HOV and NV protease. Active site residues are highlighted with downward arrows. S1 residues are highlighted with a line above them. S2 residues are highlighted with a line below them. S4 pocket residues are highlighted with a box above them. Sequences show >90% identity: SEQ ID NO:1 (top lines, HOV GII.4 protease sequence) vs. SEQ ID NO:2 (bottom lines, Norwalk Virus GI.1 Protease).

FIGS. 12A and 12B show superposition of NoV protease structures. (12A) Cartoon representations of the structures from GI genotypes GI.1 NV Pro (grey; PDB: 2FYQ), GI.4 CV Pro (orange; PDB: 1WQS) and the GII.4 HOV Pro (blue) showing the S1 and the S2 substrate-binding pockets (indicated by black arrows) on the HOV Pro undergoing conformational changes. Active site residues H30, E54, C139 (magenta), and the S2 substrate binding pocket residues R112, I109, and V114 also show structural alterations and are shown as sticks. (12B) Detailed view of the active site. Three catalytic residues H30, E54, and C139 (rendered as magenta sticks) show changes in the orientations. R112 in the GI protease structures (gray and orange sticks) is turned away from the active site. R112 in the HOV Pro structure (blue sticks) extends into the active site and interacts with H30. I109 and V114 residues in the HOV Pro also show conformational changes.

FIG. 14 provides X-ray data collection and refinement statistics.

FIG. 15 shows FRET Assay data of proteases.

FIG. 16A illustrates examples of specific inhibitors.

FIG. 17 shows examples of specific inhibitors.

FIG. 18 shows examples of specific inhibitors.

FIG. 19 shows examples of specific inhibitors.

DETAILED DESCRIPTION

Figure 1:
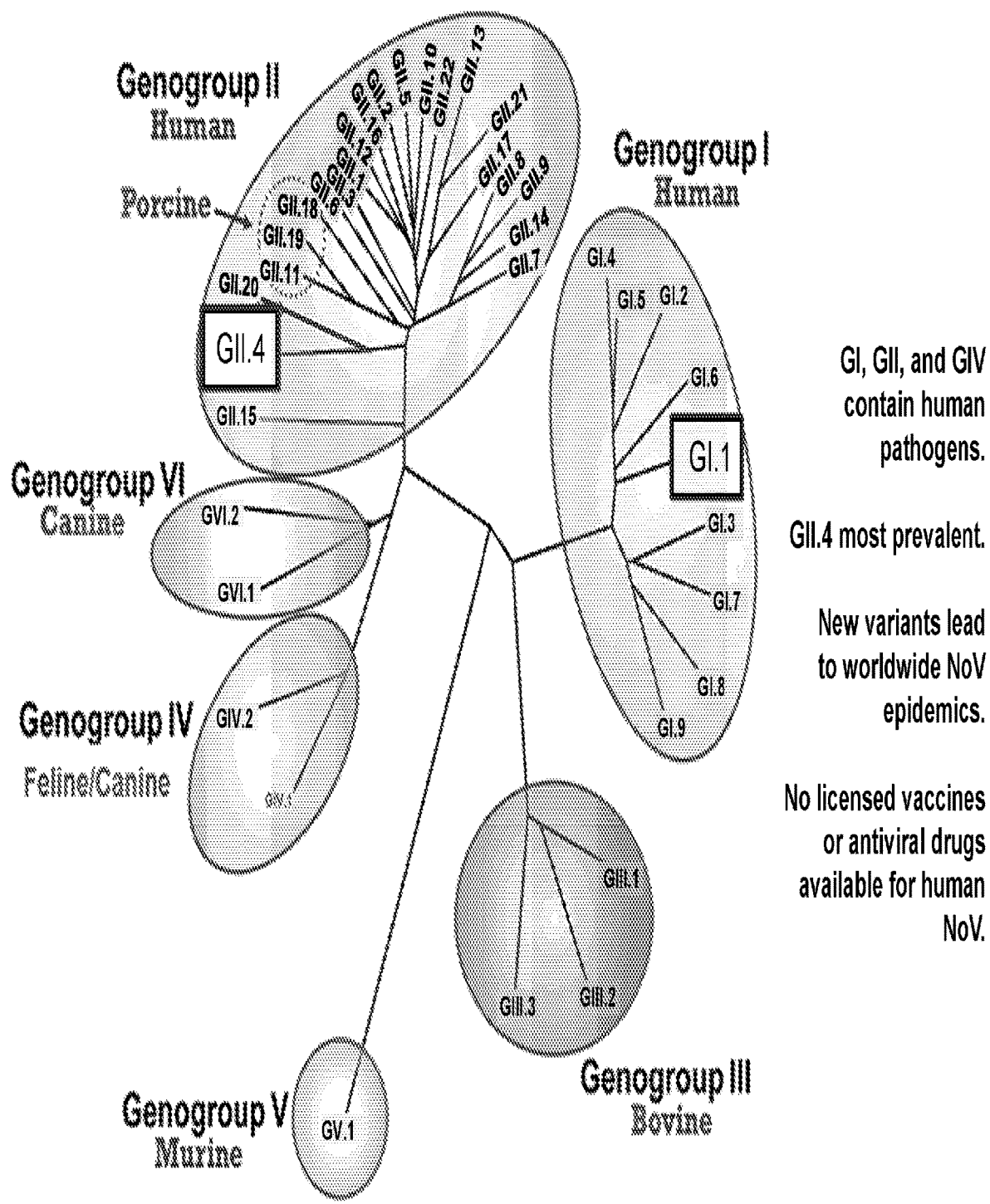
FIG. 1 illustrates Norovirus classification.
Figure 3A:
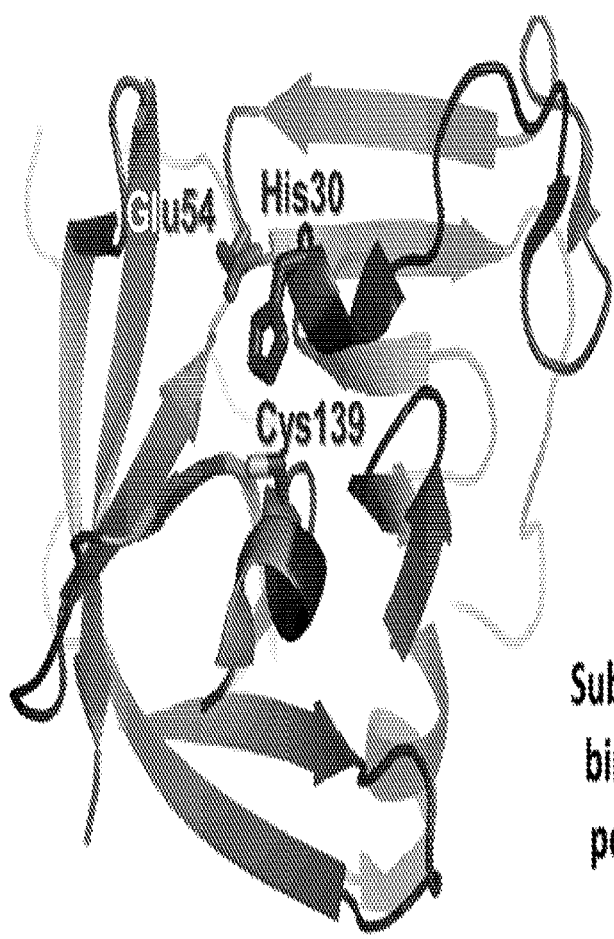
FIGS. 3A and 3B show X-ray structure of the GI.1 (NV) protease. 3A. Cartoon representation of GI.1 protease structure. Residues His30, Glu54, and Cys139 form the catalytic triad and are represented with sticks. 3B. Surface representation of the NV protease with active site shown in red and substrate binding pockets, S1 pocket in green, S2 pocket in teal, and S4 pocket in magenta. The dashed lines represent the cleft where the substrate binds.
Figure 3B:
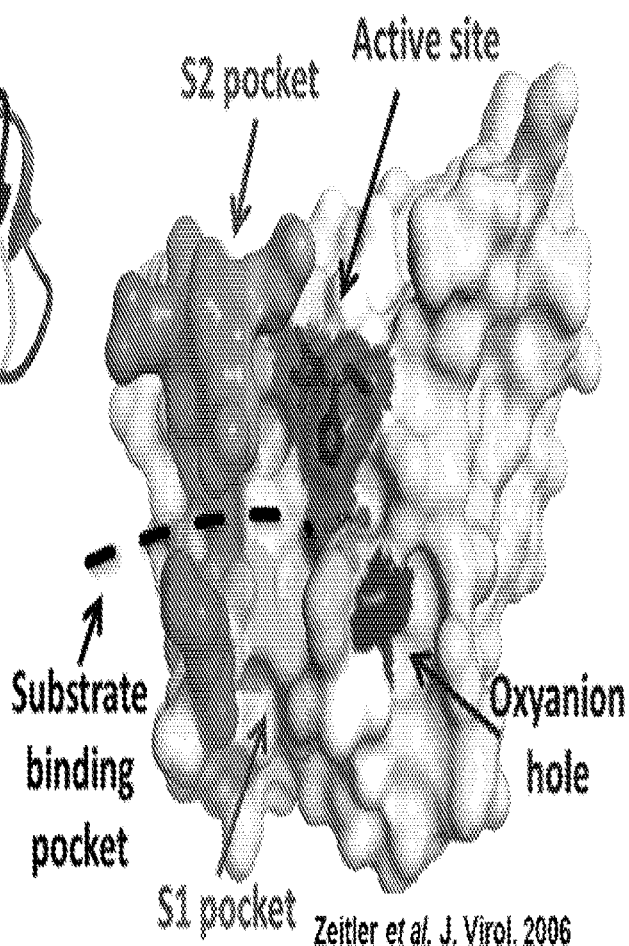
Figure 4A:
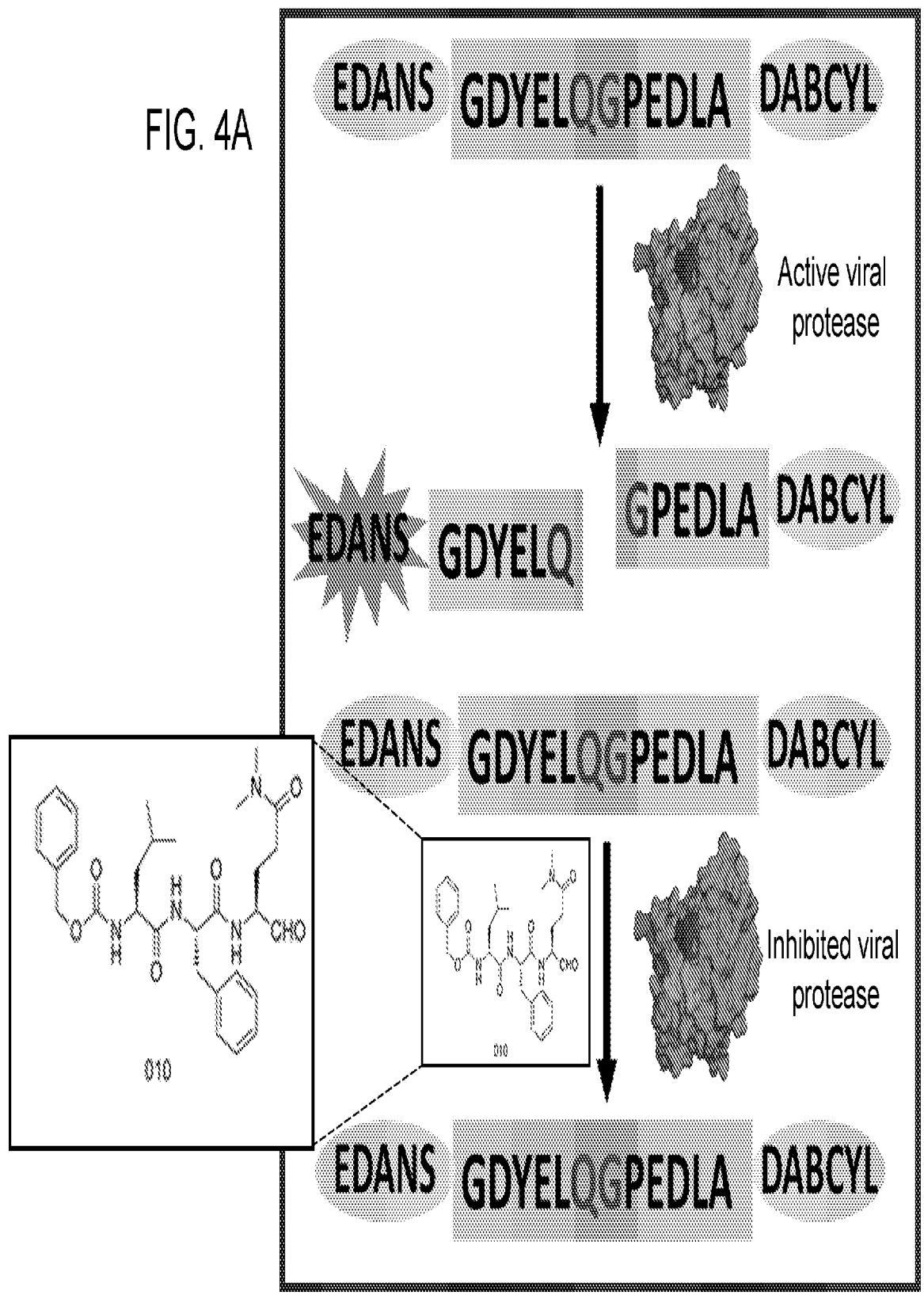
FIGS. 4A and 4B demonstrate protease activity. 4A. FRET based proteolytic assay. Fuorogenic peptide corresponds to the most efficient substrate in the polyprotein (site 1). 4B. GI.1 (NV) and GII.4 (HOV) proteases exhibit comparable proteolytic activity.
Figure 4B:
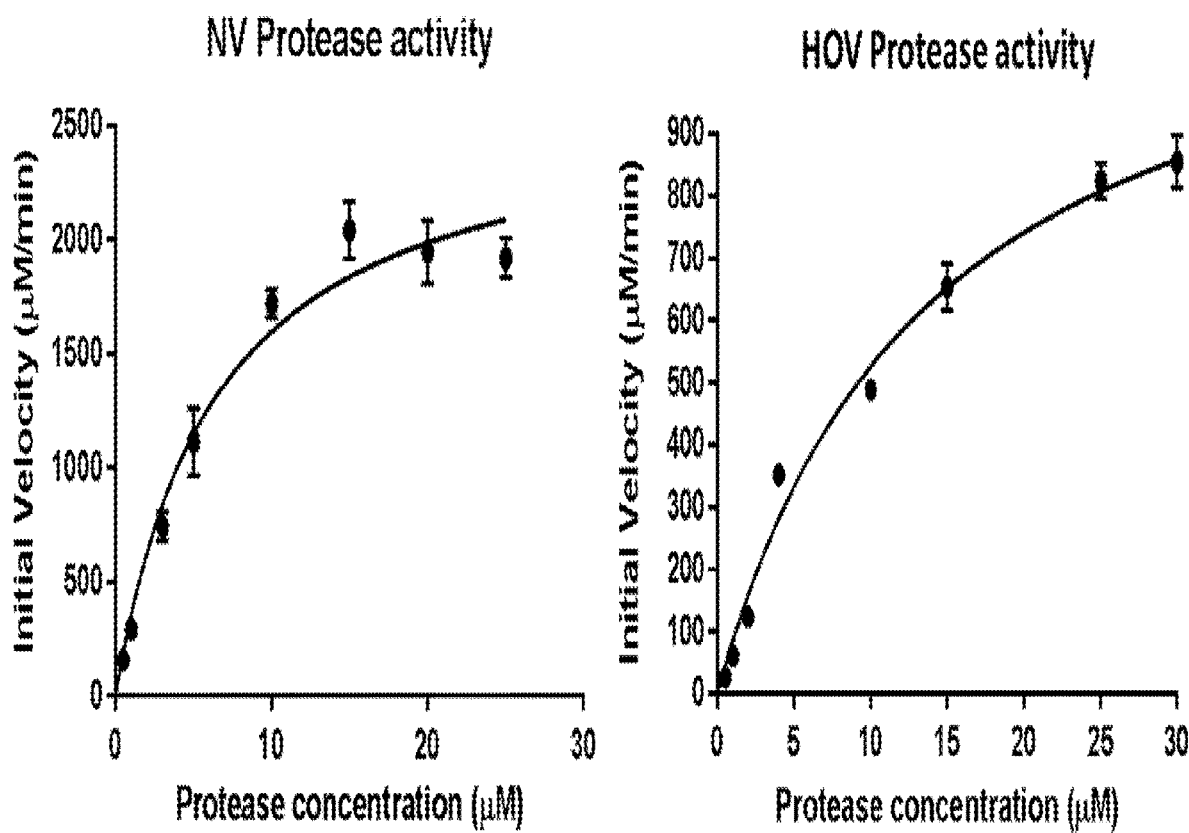
Figure 5A:
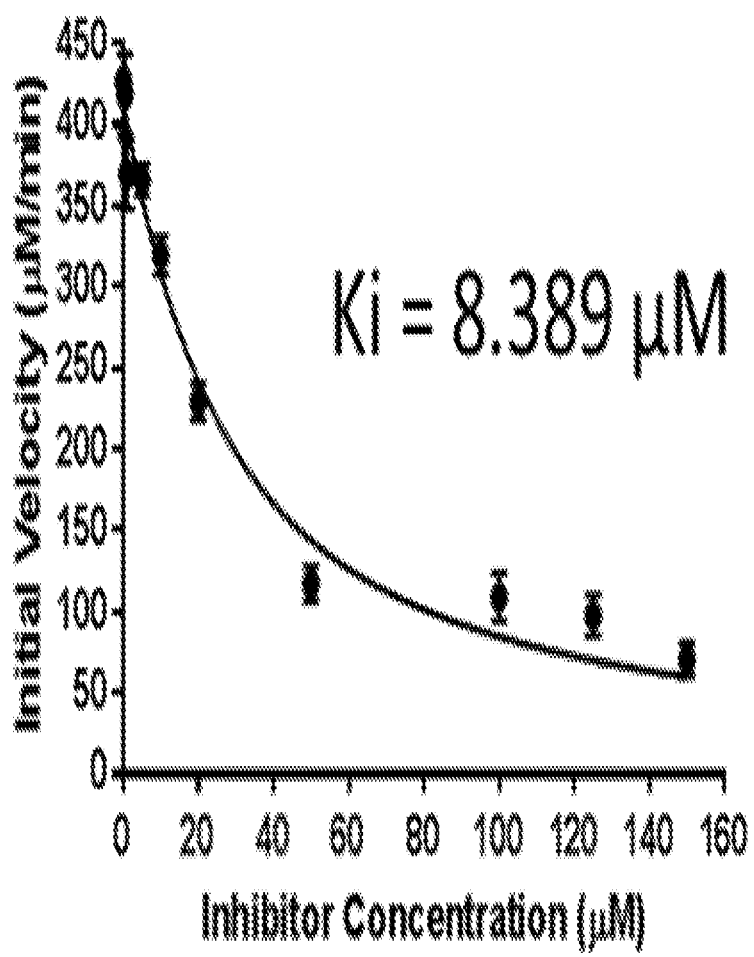
FIG. 5 demonstrates inhibition curves for three substrate-based aldehyde (syc10 and 1084) and nonaldehyde (1076) inhibitors. The protease activity decreased with the increasing inhibitor concentration. Substrate-mimicking P1-P4 residues are labeled. All three inhibitors showed less potency in inhibiting the GII.4 (HOV) protease compared to the GI.1 (NV) protease.
Figure 5B:
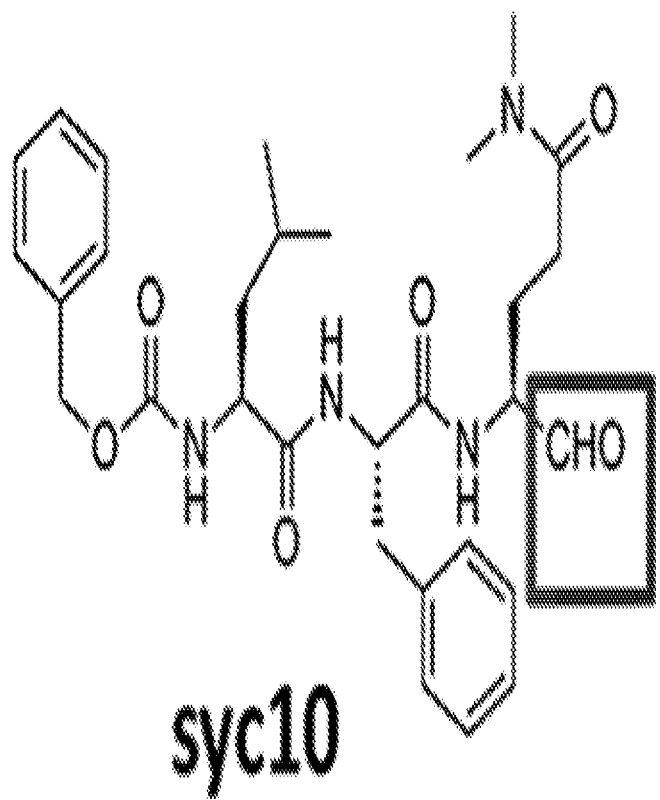
Figure 5C:
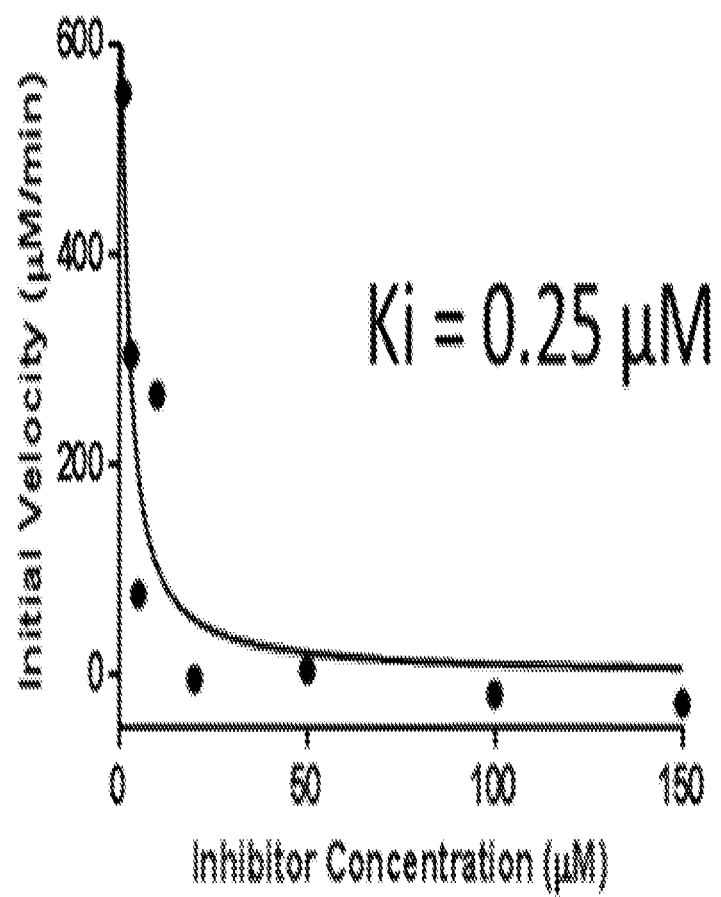
Figure 5D:
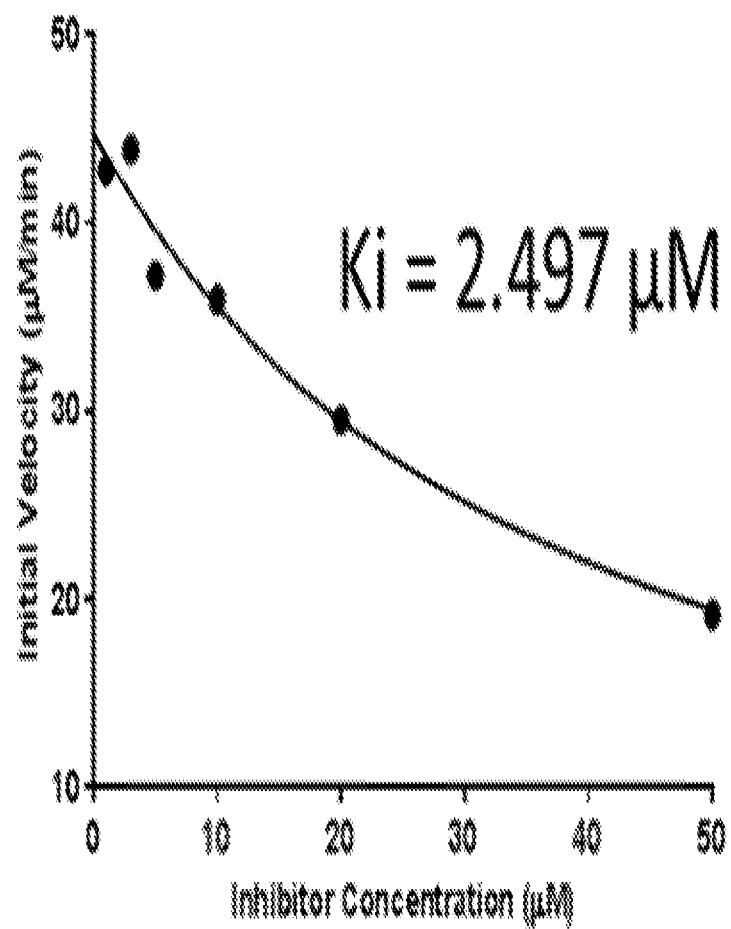
Figure 5E:
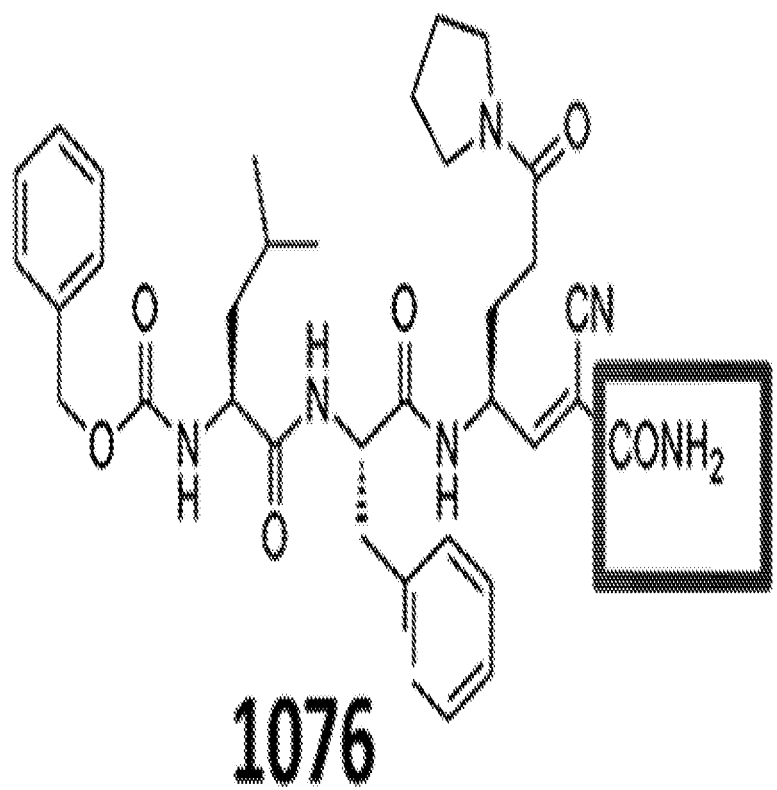
Figure 5F:
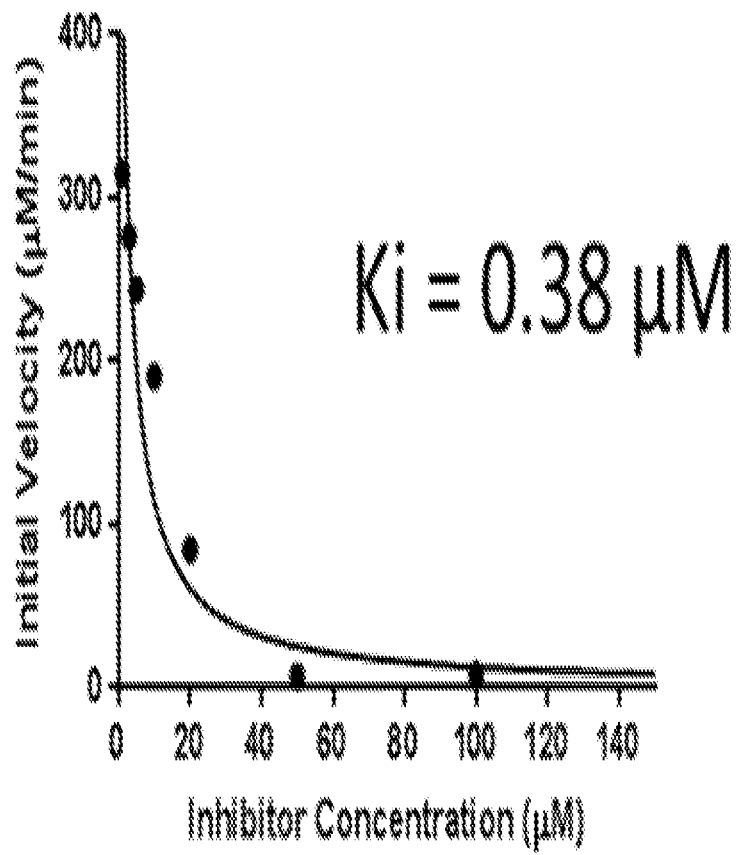
Figure 5G:
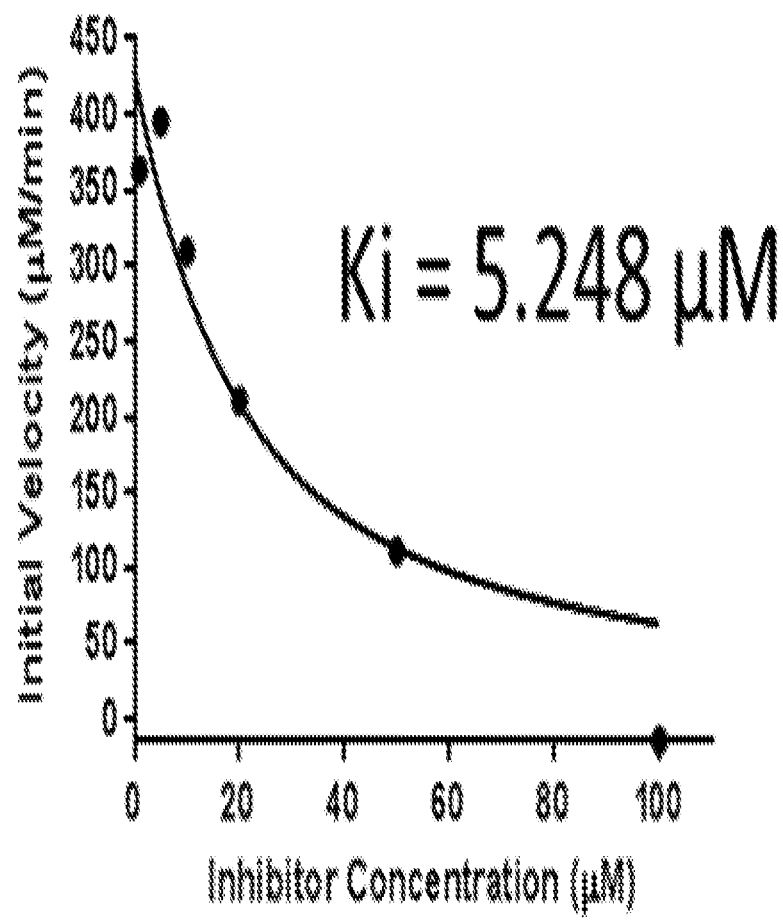
Figure 5H:
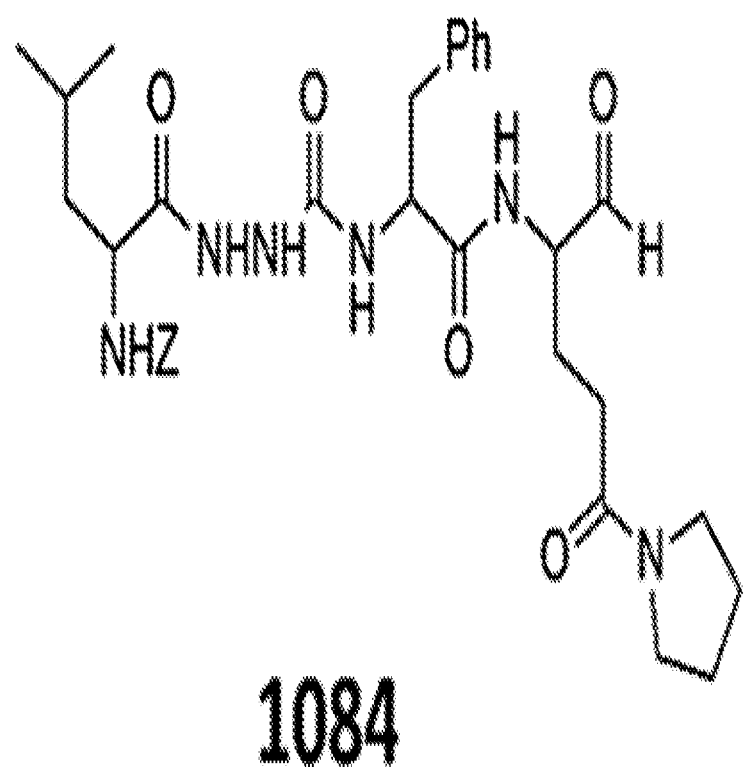
Figure 6A:
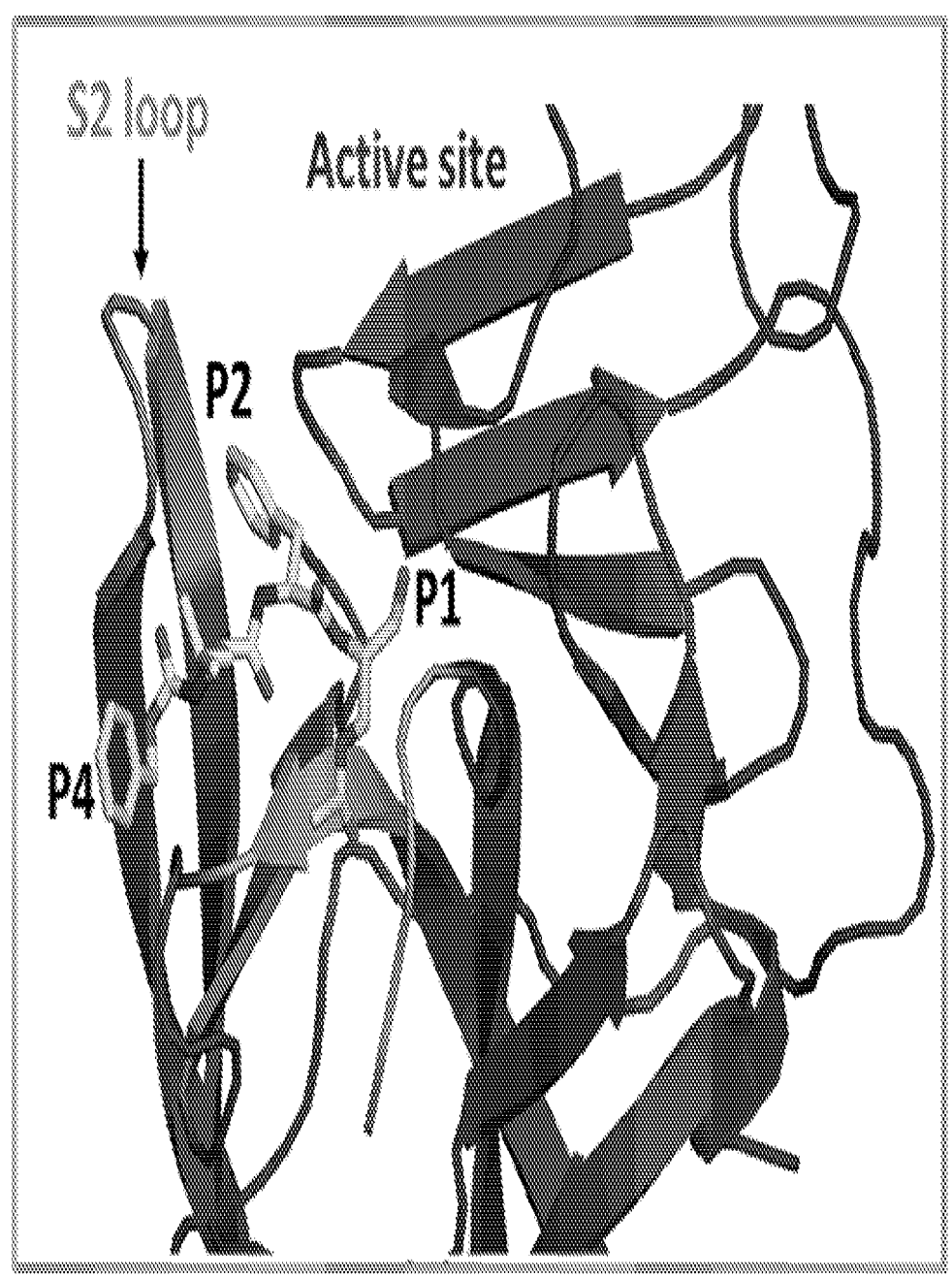
FIGS. 6A and 6B demonstrate that Syc-10 inhibitor interacts with the substrate binding pocket. 6A. Syc-10 aldehyde inhibitor (yellow sticks) bound to the active site (red) of the NV protease. The S1 pocket is shown in green and the S2 pocket is shown in cyan. 6B. Syc-10 interacting with the active site (red sticks) and binding pockets S1 (green sticks) and S2 (cyan sticks). Syc-10 forms a covalent bond with the C139 of the active site. Hydrogen bonds are represented with dashed lines.
Figure 6B:
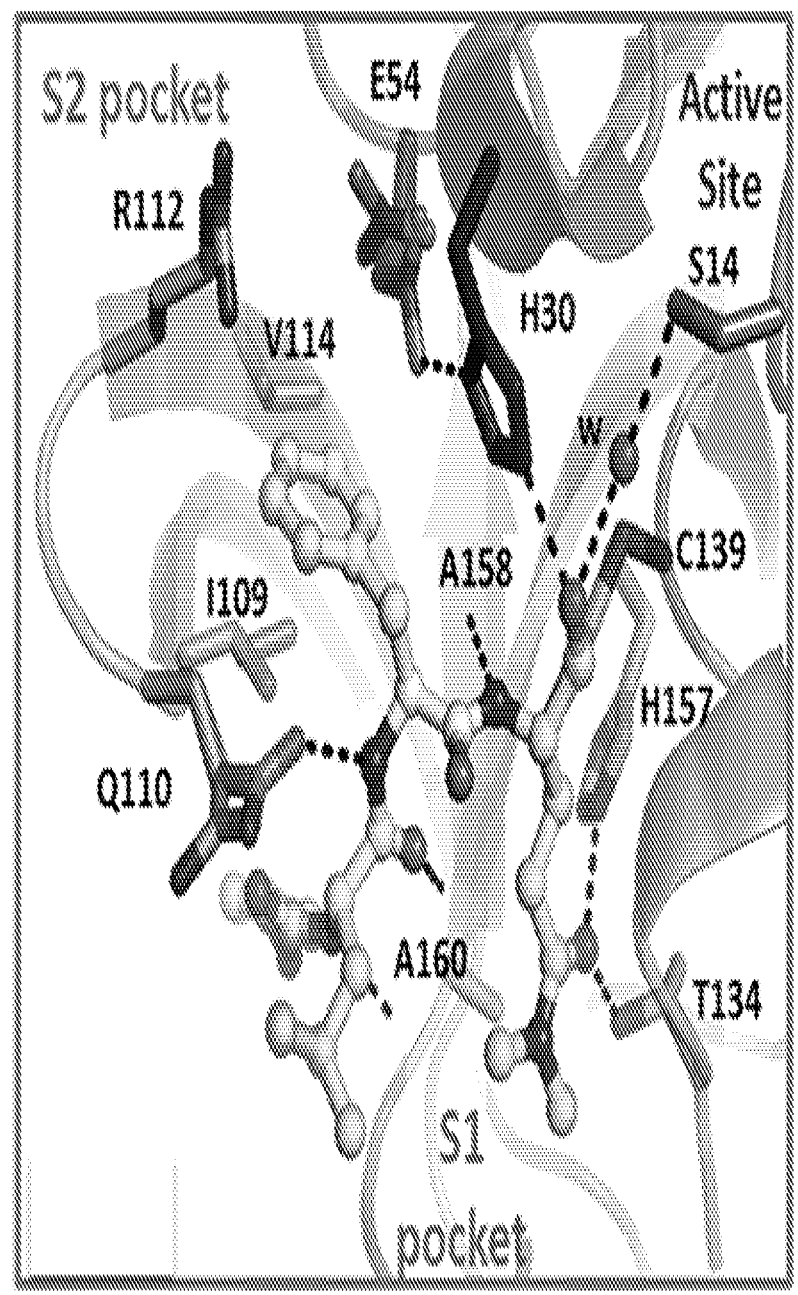
Figure 8:
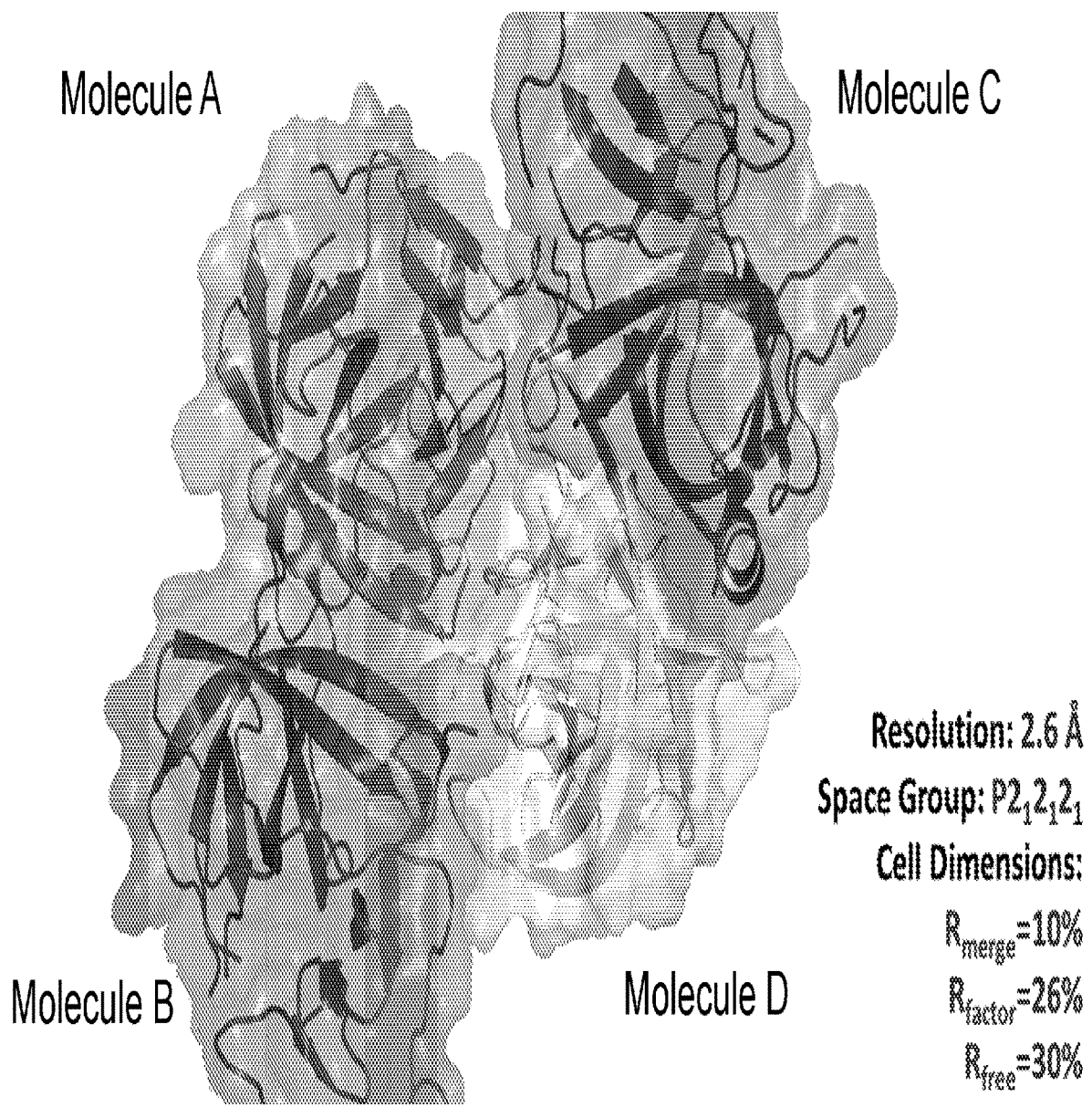
FIG. 8 provides the X-ray structure of the GII.4 protease. Crystal Packing of HOV protease in the $P2_12_12_1$ space group, with four molecules in the asymmetric unit. AB and CD dimers are shown with the crystallographic two-fold axis indicated with an arrow.
Figure 9:
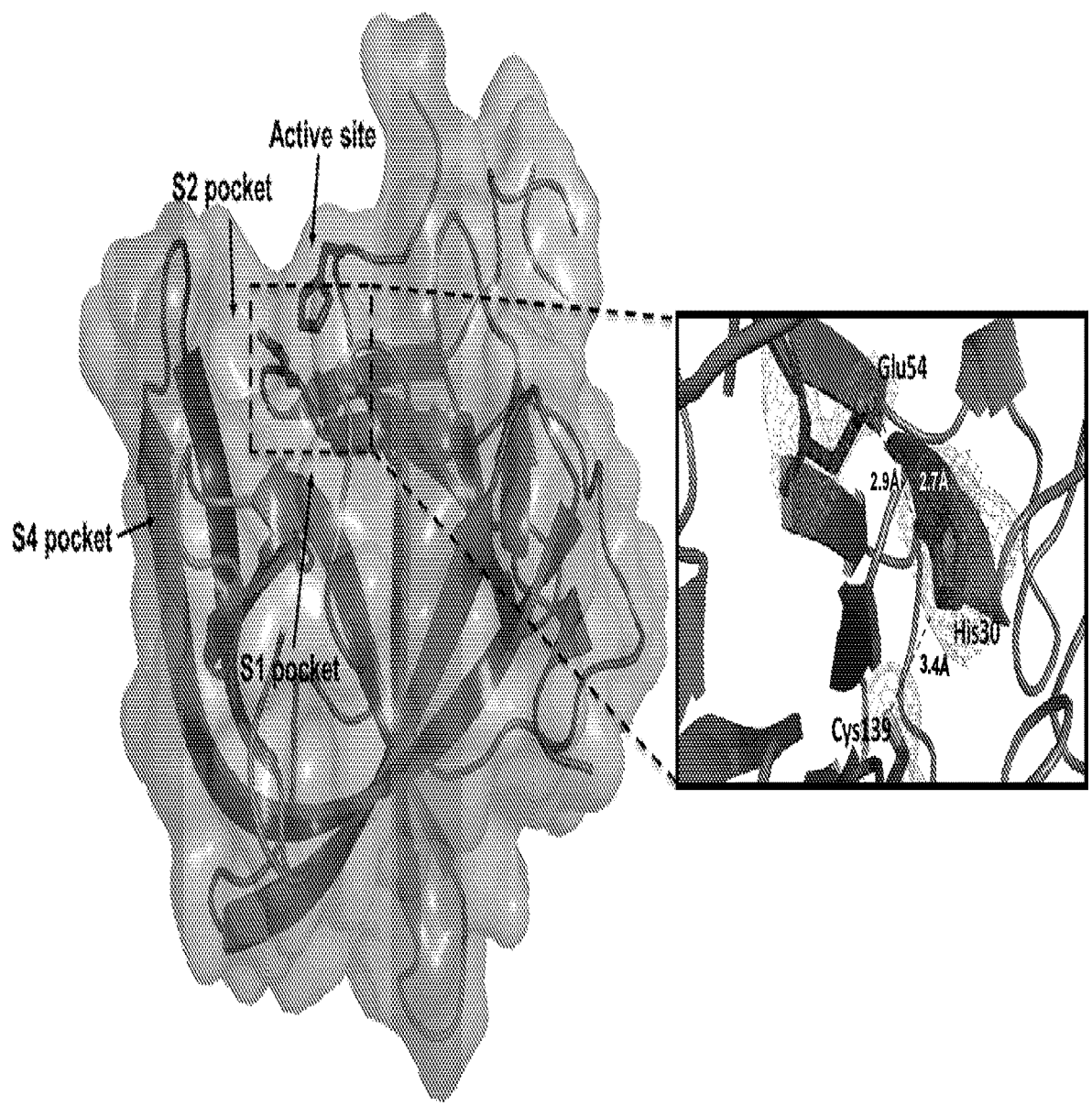
FIG. 9 shows the active site of the GII.4 protease. Protein adopts a serine protease-like fold that consists of two β-barrel domains separated by a cleft. The active site is located at the opening of the cleft and is composed to residues His30, Glu54, and Cys139 shown in red. The insert is showing the catalytic residues at 2.6 Å resolution inside the 2Fo-Fc map.
Figure 10:
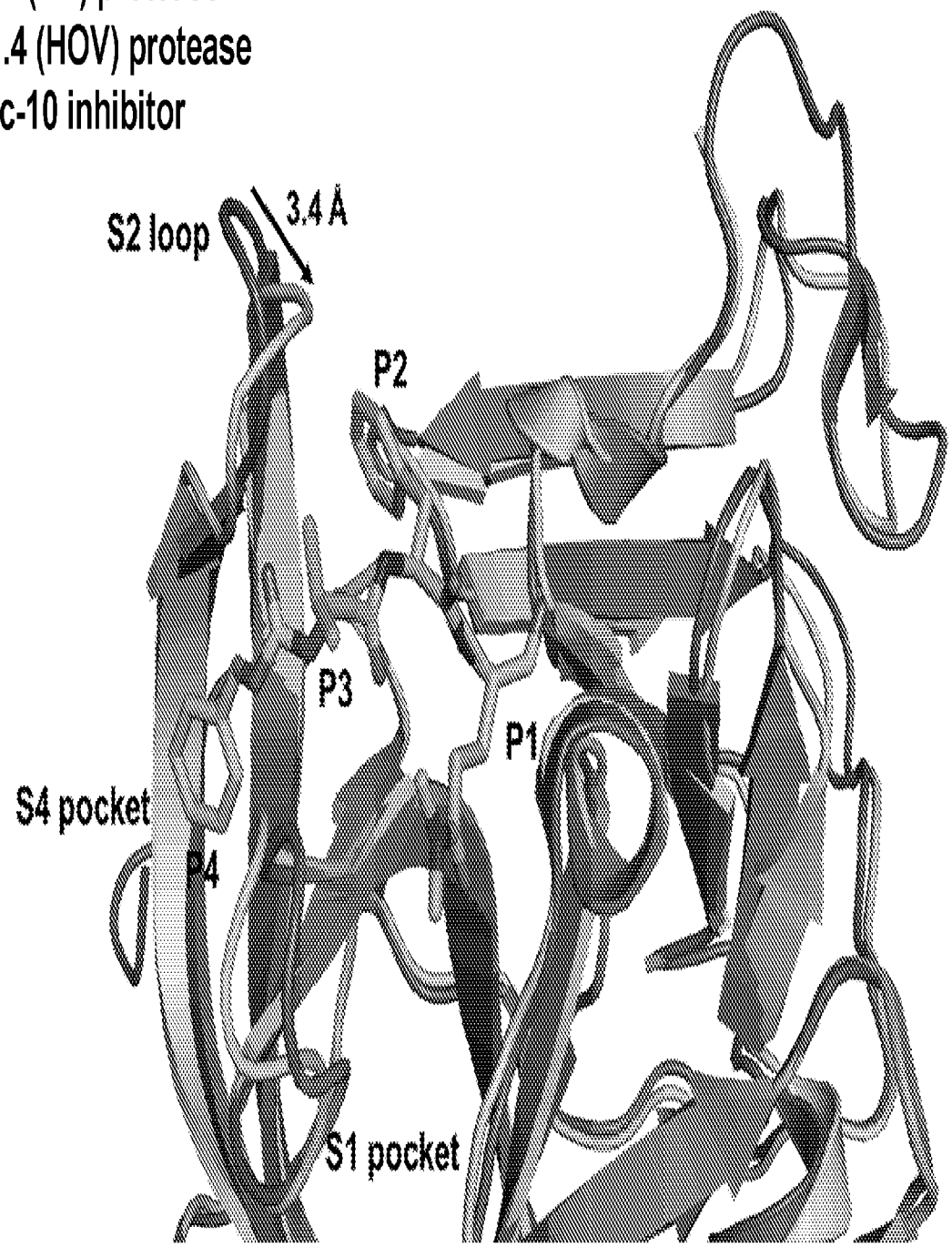
FIG. 10 demonstrates the structure superposition of the GI.1 and GII.4 protease. Although the overall structures are similar, significant changes are observed near the active site. Notably, in the GII.4-Pro structure, the loop forming the S2 pocket shows a significant deviation and moves closer to the active site. Conformational change in the S2 loop may potentially cause steric hindrance to bulky P2 residues of the GI.1-specific protease inhibitors.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Embodiments of the disclosure provide novel, broadly reactive substrate-based inhibitors against the Norovirus (NoV) protease, including as an example GII.4 protease, as an antiviral agent. Structural studies showed that the conformational changes in the loops surrounding the active site of the GII.4 protease, in particular embodiments, contribute to variance in the potency of the inhibitors. In specific embodiments, designing protease inhibitors with the smaller P2 residues is a useful strategy for developing antiviral drugs with cross-reactivity across the genotypes.

Certain embodiments of the disclosure are directed to methods of treating or preventing Norovirus infection in individuals in need thereof, including those susceptible to the infection or at risk for the infection. The individual may be at risk for the infection by having an impaired immune system or being exposed to large numbers of individuals, for example in a confined environment, such as in a school, transportation vessel (boat, plane, train), sports or entertainment venue, etc. The compositions may be provided to an individual as a precautionary measure or as a routine measure. Any individual of any age or gender may be exposed to methods and/or compositions of the disclosure.

I. Examples of Compositions

Embodiments of the disclosure include one or more small molecules that are inhibitors of Norovirus, including inhibitors of one or more Norovirus proteases. In particular embodiments, the inhibitor(s) comprise a structural configuration that facilitates inhibition of the activity of the protease. The inhibitor(s) may be a prodrug or comparable salt thereof or may be used individually or collectively with one or more antivirals or antibiotics in methods and compositions provided herein. In other embodiments, one or more compounds of one or more of the formulas below, or a prodrug or salt thereof, may be used individually or collectively with one or more antivirals or antibiotics, in methods and compositions provided herein.

Although any one of the compositions below may be utilized in methods of the disclosure, it is contemplated that in some cases one or more species may be excluded in embodiments described herein.

Examples of NoV inhibitor composition formulas, followed by specific inhibitors within the formulas, are as follows:

(Formula I)

R1 and R2 are each independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, amine, acetamidyl, or carboxybenzyl, or a diastereomer or pharmaceutically acceptable salt thereof.

SYC-796

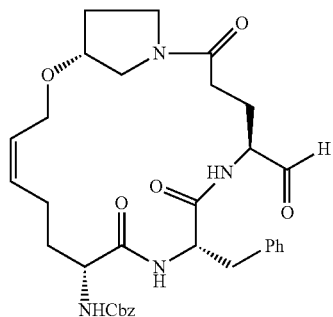

SYC-815

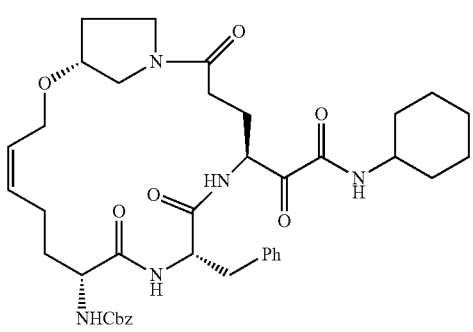

(Formula II)

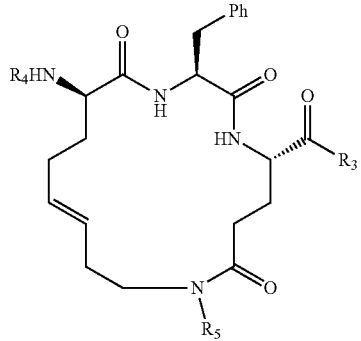

R3, R4, and R5 are each independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, amine, acetamidyl, or carboxybenzyl, or a diastereomer or pharmaceutically acceptable salt thereof.

SYC-877

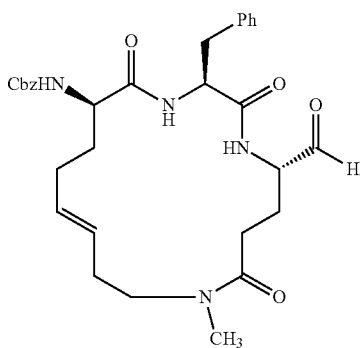

(Formula III)

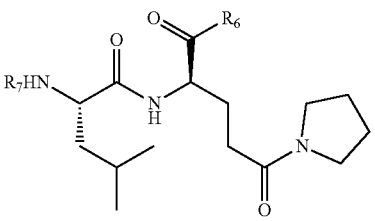

R6 and R7 are each independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, amine, acetamidyl, or carboxybenzyl, or a diastereomer or pharmaceutically acceptable salt thereof.

SYC-1075

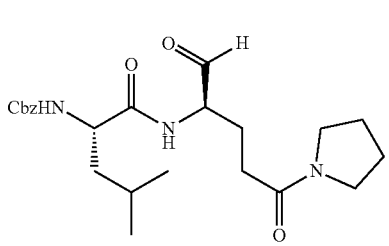

(Formula IV)

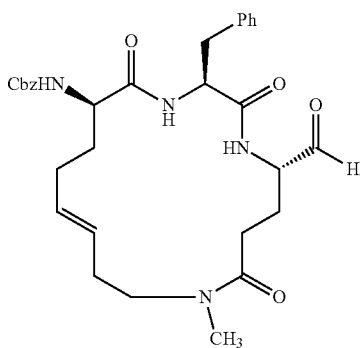

R10 is hydrogen, hydroxyl, alkoxy, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, amine, or acetamidyl.

R11 is is CHO or C(O)CH2C(O)NH2, or a diastereomer or pharmaceutically acceptable salt thereof.

SYC-1085

(Formula V)

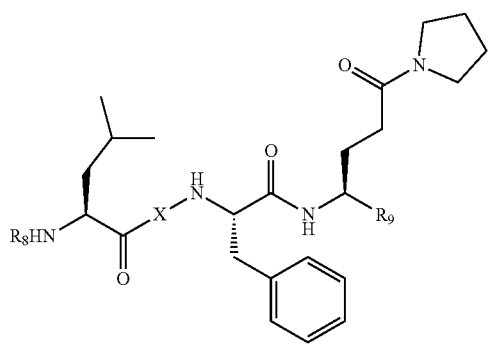

X is nothing or —NHNHC(O)—

R8 is hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, amine, acetamidyl, or carboxybenzyl.

R9 is CHO, C(O)C(O)NH-cyclohexyl, C(O)C(O)-t-Bu, C(O)CH2C(O)NH2, 3-oxiranyl-2-methyl carboxylate, or 2-cyano-3-acrylamidyl, or a diastereomer or pharmaceutically acceptable salt thereof.

SYC-1011

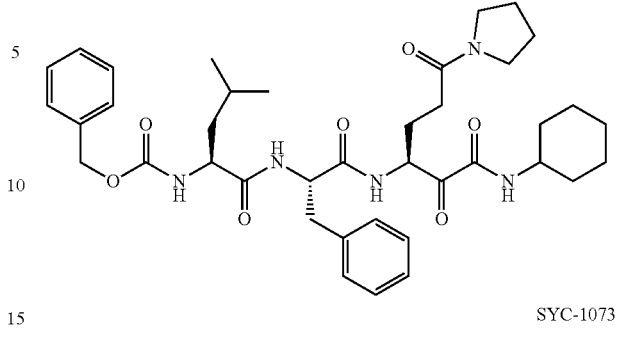

SYC-1073

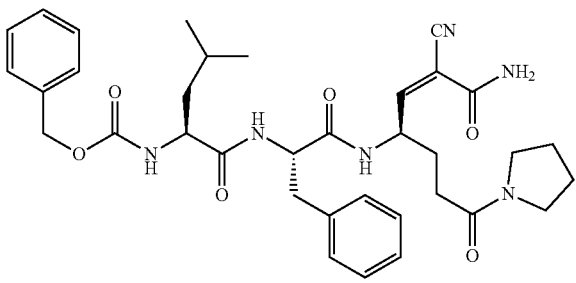

SYC-1076

SYC-1010

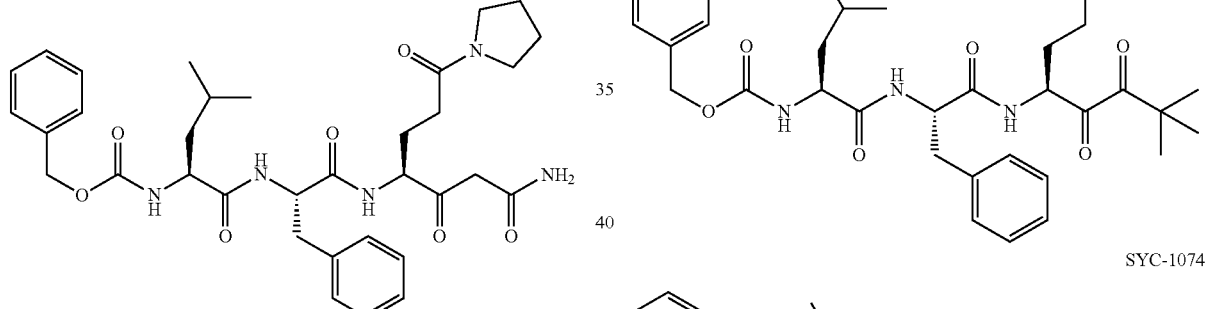

SYC-1084

SYC-1074

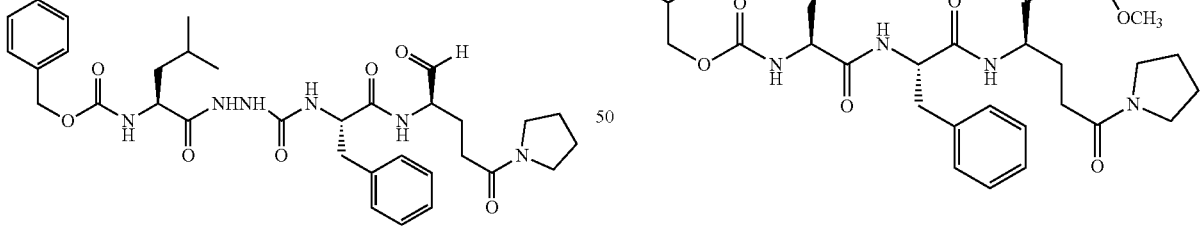

SYC-1086

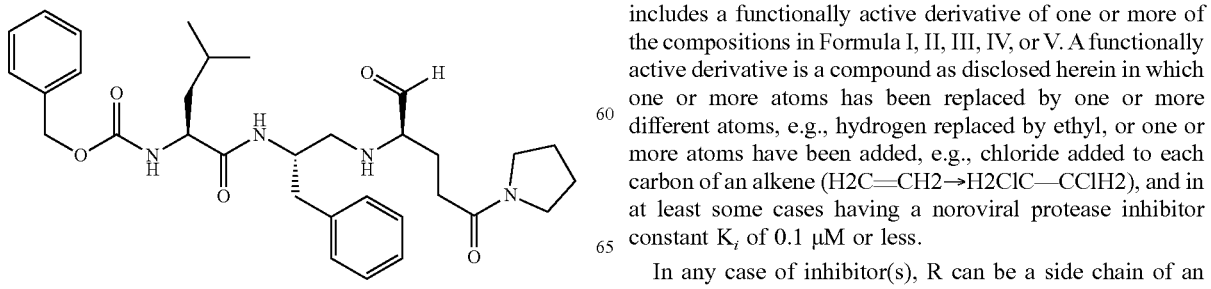

In particular embodiments, an inhibitor of the disclosure includes a functionally active derivative of one or more of the compositions in Formula I, II, III, IV, or V. A functionally active derivative is a compound as disclosed herein in which one or more atoms has been replaced by one or more different atoms, e.g., hydrogen replaced by ethyl, or one or more atoms have been added, e.g., chloride added to each carbon of an alkene (H2C═CH2→H2ClC—CClH2), and in at least some cases having a noroviral protease inhibitor constant $K_i$ of 0.1 μM or less.

In any case of inhibitor(s), R can be a side chain of an amino acid of biological origin.

One can determine whether or not a particular compound is a functionally active inhibitor of Norovirus proteases, such as with protease assays as described elsewhere herein.

The inhibitor(s) may be configured for a specific purpose. In some cases, one or more inhibitors are configured as a pharmaceutical composition, such as being within a pharmaceutically acceptable excipient, and/or one or more inhibitors may be configured as a cleaning composition. The inhibitor(s) may be configured as an immunogenic composition, including a vaccine, for example. In pharmaceutical compositions, the composition may be formulated in a cream, solution, pill, tablet, suppository, film, or enema. In a cleaning composition, the composition may be formulated as a solution or cream. In specific cases, the inhibitor(s) may be comprised in a composition that is in and/or on a substrate, such as a towel, wipe (including baby and/or medical wipes), or sponge.

II. Examples of Methods of Use

A variety of methods and compositions are contemplated for inhibiting, preventing, or treating a Norovirus infection using one or more compositions, such as one or more compositions that inhibits a Norovirus protease. The Norovirus may be of any kind.

The composition(s) of the disclosure may be utilized for treatment of Norovirus infection or for protection against Norovirus infection. The composition(s) may improve one or more symptoms of Norovirus infection. In some cases, one or more of the inhibitors reduces the severity of one or more symptoms of Norovirus infection and/or delays onset of Norovirus infection and/or decreases the duration of one or more symptoms of Norovirus infection.

Compositions described herein may be utilized in the treatment or prevention of Norovirus infection for any mammal, including at least a human, dog, cat, horse, pig, sheep, goat, and so forth, and/or for treatment of an environment. In some cases, the compositions are useful for the treatment or prevention of any genotype of Norovirus, although in some cases the compositions are useful for the treatment, prevention, and/or diagnosis of a particular genotype or genogroup or sub-combination of genotypes or genogroups. In specific embodiments, the compositions are useful at least for Norovirus genotype GII.4, for example.

In at least some cases, compositions, or mixtures thereof (including mixtures of different compositions each of which may or may not target a protease from a different Norovirus genotype), are delivered prior to and/or following exposure of an individual to large populations of individuals or environments prone to Norovirus infection, including confined environments. Such environments include passenger vessels, including cruise ships, airplanes, and trains; schools; arenas (sports and/or music, for example); military environments, such as military encampments; health care facilities, including nursing homes, hospitals, and long-term care facilities; food service settings, such as restaurants and catered events; child care centers; prisons; recreational water settings; lodging facility (such as hotels or motels); and so forth. The compositions may be additionally or alternatively provided to an individual in the course of routine preventative measures.

In some embodiments of the disclosure an individual is provided one or more composition(s) for the prevention of Norovirus infection. In specific embodiments, individual compositions are effective for one genotype, and therefore an individual is given a plurality of compositions, each specific for or more effective for a Norovirus genotype. In specific embodiments, an individual is given the composition(s) in multiple administrations, including through booster deliveries, in at least some cases.

Any of the compositions and methods of using these compositions can treat a subject having, suspected of having, or at risk of developing a Norovirus infection or related disease. One use of the compositions is to prevent infections by inoculating a subject prior to exposure to Norovirus.

In some cases, the method includes steps that identify an infection or exposure as being Norovirus, and such method steps may or may not utilize the compositions of the disclosure. A biological sample from an individual for analysis in methods of the disclosure may comprise stool, vomitus, saliva, serum, plasma, or tissue specimens for histopathology such as intestinal biopsy specimens. In some embodiments, food (for example, shellfish, including mollusks such as oysters, clams, mussels and scallops), water, and/or environment samples (including swabs of environmental surfaces) are tested for the presence of Norovirus, for example using antibodies that immunologically recognize Norovirus.

An individual being treated or in need of treatment will typically have (e.g., diagnosed with a Norovirus infection), be suspected of having, or be at risk of developing a Norovirus infection. Compositions include Norovirus protease-binding small molecule(s) in amounts effective to achieve the intended purpose—treatment or protection of Norovirus infection. More specifically, an effective amount means an amount of active ingredients necessary to provide resistance to, amelioration of, or mitigation of infection. In more specific aspects, an effective amount prevents, alleviates or ameliorates one or more symptoms of disease or infection, or prolongs the survival of the subject being treated. Determination of the effective amount is well within the capability of those skilled in the art, especially in light of the detailed disclosure provided herein. For any preparation used in the methods described herein, an effective amount or dose can be estimated initially from in vitro, cell culture, and/or animal model assays. For example, a dose can be formulated in animal models to achieve a desired response. Such information can be used to more accurately determine useful doses in humans.

In certain embodiments, there is a method for treating a Norovirus infection comprising the step of administering an effective amount of a composition encompassed by the disclosure that specifically binds a targeted region of the protease to an individual having or suspected of having a Norovirus infection. In some embodiments, an individual may also be treated for dehydration, including oral rehydration fluids and/or intravenous fluids. In some cases, the dose of composition delivered to the individual a dose of 0.1, 0.5, 1, 5, 10, 50, 100 mg or µg/kg to 5, 10, 50, 100, 500 mg or µg/kg. In specific embodiments, the composition is delivered to the individual via a route that is intravenous, intramuscular, rectal, and/or oral, as examples.

Certain aspects are directed to methods of preventing or treating Norovirus infection comprising administering to an individual having or suspected of having a Norovirus infection an effective amount of one or more compositions that specifically bind the protease of a Norovirus.

Certain aspects are directed to methods of treating a subject having or suspected of having a Norovirus infection comprising administering to an individual having or suspected of having a Norovirus infection an effective amount of one or more compositions encompassed by the disclosure. In a further aspect methods are directed to treating a subject at risk of a Norovirus infection comprising administering to a patient at risk of a Norovirus infection an effective amount of one or more compositions encompassed by the disclosure prior to infection with Norovirus.

The subject typically will have (e.g., diagnosed with a Norovirus infection), will be suspected of having, or will be at risk of developing a Norovirus infection. Compositions include certain small molecules in amounts effective to achieve the intended purpose—treatment or protection of Norovirus infection. More specifically, an effective amount means an amount of active ingredient(s) necessary to provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods described herein, an effective amount or dose can be estimated initially from in vitro, cell culture, and/or animal model assays, for example. For example, a dose can be formulated in animal models to achieve a desired response. Such information can be used to more accurately determine useful doses in humans.

There is encompassed herein a method of treating an individual for Norovirus infection or preventing Norovirus infection in an individual, comprising the step of providing to the individual a therapeutically effective amount of one or more compositions of the disclosure. Any of the compositions and methods of using these compositions can treat a subject having, suspected of having, or at risk of developing a Norovirus infection or related disease. One use of the compositions is to prevent infections by inoculating a subject prior to exposure to Norovirus.

One use of the compositions of the disclosure is to prophylactically treat a subject for Norovirus, such as in the early or late stages of infection, by inoculating an individual, particularly once a risk of developing disease from Norovirus infection has been foreseen or indicated. In certain aspects, a "risk" means symptoms being presented or the individual having been present environment where Norovirus has been detected or is suspected of being present.

In one embodiment a method includes treatment for a disease or condition caused by a Norovirus pathogen. In certain aspects embodiments include methods of treatment of Norovirus infection, such as hospital-acquired nosocomial infections. In some embodiments, the treatment is administered in the presence of Norovirus antigen(s). Furthermore, in some examples, treatment comprises administration of other agents commonly used against infection, such as bacterial infection, for example, one or more antibiotics.

The therapeutic composition(s) are administered in a manner compatible with the dosage formulation, and in such amount as will be therapeutically effective. The quantity to be administered depends on the subject to be treated. Precise amounts of active ingredient(s) required to be administered depend on the judgment of the practitioner. Suitable regimens for initial administration and boosters are also variable, but are typified by an initial administration followed by subsequent administrations.

The manner of application may be varied widely. Any of the conventional methods for administration of a therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, or 12 or more week intervals, including all ranges there between.

In one aspect, it is contemplated that the therapy of the disclosure is used in conjunction with a different antiviral treatment. Alternatively, the therapy may precede or follow the other agent treatment by intervals ranging from minutes to weeks. In embodiments where the other agents and/or a proteins or polynucleotides or antibodies are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Administration of the compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

In some embodiments, a composition contains about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or mg/ml or µg/ml of a substance identified above, or a combination of substances or components, or any range derivable therein.

The concentration of a composition in a formulation can be about, at least about or at most about 0.001, 0.01, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml, including all values and ranges there between. In certain aspects the dose range is 0.01 to 500 mg/kg, 10 to 300 mg/kg, or 0.01 to 10 mg/kg. About, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be a composition of the disclosure.

Delivery of any composition for therapeutic purpose may occur by any suitable regimen, including being administered more than one time to the subject, and they may be administered 1, 2, 3, 4, 5, 6, 7, 8, 9, 10, 15, 20 or more times. The route of administration of the compositions includes, but is not limited to oral, parenteral, subcutaneous and intravenous administration, rectal, or various combinations thereof, including inhalation or aspiration. In certain instances, it will be desirable to have multiple administrations of the composition, e.g., 2, 3, 4, 5, 6 or more administrations. The administrations can be at 1, 2, 3, 4, 5, 6, 7, 8 to 5, 6, 7, 8, 9, 10, 11, 12 day or week intervals, including all ranges there between.

In some embodiments, one or more of the compositions are utilized for treatment of an environment that is infected with Norovirus or has the potential to be infected with Norovirus. In some examples, the environment may be one subject to large populations of individuals, including confined environments. Such environments include transportation or passenger vessels, including cruise ships, airplanes, and trains; schools; arenas; military environments, such as military encampments; health care facilities, including nursing homes, hospitals, and long-term care facilities; food service settings, such as restaurants and catered events; child care centers; prisons; recreational water settings; convention centers; lodging facilities, such as hotels and motels; shopping centers, such as malls, and so forth. In such cases, one or more surfaces in the environments may be treated with one or more of the inhibitors. The inhibitor(s) may or may not be included in a formulation with other viral inhibitors or other pathogen (bacterial and/or fungal, for example) inhibitors. In certain formulations, the inhibitor may be a particular percentage in the formulation, such as at least or no more than 0.01, 0.05, 0.1, 0.5, 0.75, 1, 5, 10% or more in the formulation. Any formulation that includes the inhibitor(s) may or may not be applied to a surface in an environment at regular intervals in time.

III. Pharmaceutical Compositions

In some embodiments, pharmaceutical compositions are administered to a subject. Different aspects may involve administering an effective amount of a composition to a subject. In some embodiments, protease inhibitor that directly or indirectly binds Norovirus may be administered to the subject to protect against or treat infection by Norovirus. Additionally, such compositions can be administered in combination with one or more antibiotics. Such compositions can generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition(s) also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions are administered in a manner compatible with the dosage formulation and in such amount as is therapeutically or prophylactically effective. The formulations are easily administered in a variety of dosage forms, such as the type of injectable solutions described above.

IV. Kits of the Disclosure

Any of the compositions described herein may be comprised in a kit. In a non-limiting example, one or more compositions for Norovirus treatment or prevention may be comprised in a kit in suitable container means. The kit may be utilized for the treatment of Norovirus infection and/or for the prevention of Norovirus infection and/or for detection of Norovirus, including from a mammalian sample(s) and/or one or more environments. In specific embodiments, the kit comprises certain small molecules encompassed by the disclosure.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the Norovirus composition and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The Norovirus compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The kits of the present disclosure will also typically include a means for containing the vials in close confinement for commercial sale, such as, e.g., injection and/or blow-molded plastic containers into which the desired vials are retained.

In some cases, the kit includes one or more antiviral or antibiotic compositions in addition to the inhibitor(s) of the present disclosure. Some kits may include a pharmaceutical composition and/or a cleaning composition.

In certain embodiments, the kit comprises one or more apparatuses and/or reagents for obtaining a sample from an individual and/or processing thereof.

EXAMPLES

The following examples are given for the purpose of illustrating various embodiments and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Structure of GII.4 Norovirus Protease—Design of Broad-Spectrum Protease Inhibitors The crystal structures were determined of the Norwalk virus (GI.1) protease (GI.1-Pro) in complex with substrate-based inhibitors that mimic the P1-P4 residues, wherein the inhibitors have an aldehyde warhead that target the active site of the GI.1-Pro. They inhibit protease activity by forming a covalent adduct and preventing the conformational changes within the active site. These inhibitors, when tested against the protease of a GII.4 variant (GII.4-Pro; Houston virus), showed reduced activity. To characterize this difference, the inventors determined the crystal structure of the GII.4-Pro and compared it with GI.1-Pro structure. Although the overall structures are similar, there were significant changes near the active site. Notably, in the GII.4-Pro structure, the loop forming the S2 pocket shows a significant deviation and moves closer to the active site. In specific embodiments, this conformational change causes steric hindrance, not allowing the S2 pocket to accommodate bulky P2 residues of the GI.1-specific inhibitors. The results indicate that designing protease inhibitors with the smaller P2 residues would be a useful strategy for developing the antiviral drugs with cross-reactivity across the genotypes.

Example 2

GII.4 Norovirus Protease Shows pH-Sensitive Proteolysis with A Unique Arg-his Pairing in the Catalytic Site In the present example, the crystal structure of a GII.4 protease, namely the Houston virus protease (HOV Pro), was determined and was compared with the available GI protease structures. The studies show that, although the overall structure of HOV Pro is conserved, there are several significant changes in the orientation of residues comprising the active site. The side chain of an arginine residue (R112) is found inserted in the active site of the HOV Pro making interactions with the catalytic H30 residue. The studies indicate a pH-dependent role for R112 in modulating substrate and inhibitor binding to the HOV Pro. Overall the results provide a structural framework for structure-based drug design of broadly cross-reactive inhibitors targeting NoVs.

Examples of Materials and Methods

Protein expression and purification. Both NV and HOV Pro were cloned into the bacterial pET-46 Ek/LIC expression vector (Qiagen, Hilden, DE) with the N-terminal 6xHis tag followed by a thrombin cleavage site (LVPRGS), as described by Zeilter et al., 2006. The proteins were expressed in *Escherichia coli* BL21 (DE3) cells (Novagen, EMD Biosciences, Inc., Darmstadt, Del.) and purified using Ni-nitrilotriacetic acid (Ni-NTA) affinity chromatography resin (Qiagen). Following Ni-NTA purification the 6xHis tags were cleaved off by using thrombin (Haematologic Technologies, Inc., Essex Junction, Vt., USA) and proteins were further purified by gel filtration chromatography (HiLoad 16/60 Superdex 75; GE Healthcare, Little Chalfont, UK). Purified NV and HOV Pro were concentrated to 18 mg/mL and 20 mg/mL, respectively, and stored in 50 mM $NaH_2PO_4$ (pH 8), 100 mM NaCl, and 5 mM TCEP [tris(2-carboxyethyl)phosphine)] buffer until further use. The R112A mutant was generated by Epoch Life Science, Inc. (Sugar Land, Tex., USA) and expressed in the BL21 (DE3) cells and purified as described above.

Crystallization of the HOV protease. The HOV Pro was concentrated to ~6 mg/mL and crystallized by the hanging drop vapor diffusion method using the Mosquito crystallization robot (TTP LabTech, Herts, Melbourn, UK) at 20° C. Final crystals were obtained in 0.2 M Potassium thiocyanate, 0.1 M Bis-Tris propane (pH 6.5), 20% (w/v) PEG 3350, placed in the cryoprotectant solution (20% glycerol), and flash-frozen in liquid nitrogen.

Data collection and processing. A complete data set was collected to a resolution of 2.6 Å at the Argonne National Laboratory Advanced Photon Source, beamline SBC-19ID (Chicago, Ill., USA). The diffraction data were collected using 1.0° oscillation angle and integrated using XDS (Kabsch, 2010). HOV Pro crystallized in the space group P212121 with four molecules in the asymmetric unit. The previously determined structure of NV protease (PDB 4IN1) (Muhaxhiri, et al., 2013) was used for phasing, using the molecular replacement (MR) program PHASER (McCoy, et al., 2007) as implemented in the CCP4 suite of programs (Collaborative Computational Project No., 1994). Following the manual adjustment of the initial model in COOT (Emsley, et al., 2004), iterative cycles of refinement and further model building were carried out using PHENIX (Adams, et al., 2002) and COOT programs. During the course of the refinement, and following the final refinement, the stereochemistry of the structures was checked using Molprobity (http://molprobity.biochem.duke.edu/). Data refinement and statistics are given in FIG. 14. Figures were prepared using PyMOL.

Protease activity and inhibition assays. The activity of the purified NV Pro and HOV Pro was confirmed by using a Fluorescence Resonance Energy Transfer (FRET) assay as described previously (Zeitler, et al., 2006; Muhaxhiri, et al., 2013). Fluorogenic peptides Glu(EDANS)-GDYELQG-PEDLA-Lys(Dabcyl) and Glu(EDANS)-EPDFLQGPED-LAK-Lys(Dabcyl) corresponding to the natural cleavage sites between p48 and p41 in the HOV and NV polyproteins, respectively, were synthesized by GenScript USA Inc. (Piscataway, N.J., USA) with the fluorescent dye (EDANS) at the N-terminal of the peptide and the quencher (Dabcyl) at the C-terminal. When the peptide is cleaved by the protease, the dye is no longer quenched, resulting in an increase in fluorescence. The assays were performed in 50 mM $NaH_2PO_4$ (pH 8, 6.5, or 5), 100 mM NaCl, and 5 mM TCEP buffer. Increasing concentrations (1, 2, 4, 8, 15, 30, 45, 60, 100, and 150 µM) of the substrate were added to 1 µM of the protease and the fluorescence was measured at excitation/emission wavelengths of 360 nm and 465 nm using the DTX 880 Multimode Detector (Beckman Coulter, Inc., Brea, Calif., USA). Fluorescence signal was monitored for 120 min at 90 sec intervals at 37° C. The Relative Fluorescent Units (RFUs) were converted to the product formed in µM, using a standard curve. Initial velocities, Michaelis constants ($K_m$), and the catalytic constant ($k_{cat}$) were calculated using the non-linear regression analysis using GraphPad Prism 7 software (GraphPad Software, Inc., La Jolla, Calif., USA). For the inhibition assays, Syc-10 and Syc-59 aldehyde inhibitors were synthesized previously as described by Deng et al., 2013. HOV Pro R112A (2.5 µM) was mixed with increasing concentrations (0, 0.2, 0.5, 1, 3, 5, 10, 20, 50, 100, 150, and 300 µM) of the inhibitor and incubated at room temperature for 30 min prior to addition of the 30 µM substrate. Upon addition of the substrate, the change in the fluorescent signal was measured immediately as described above. Inhibition constants ($K_i$) were calculated by nonlinear curve fit into the non-competitive mode of inhibition using the GraphPad software.

Examples of Results

Figure 11A:
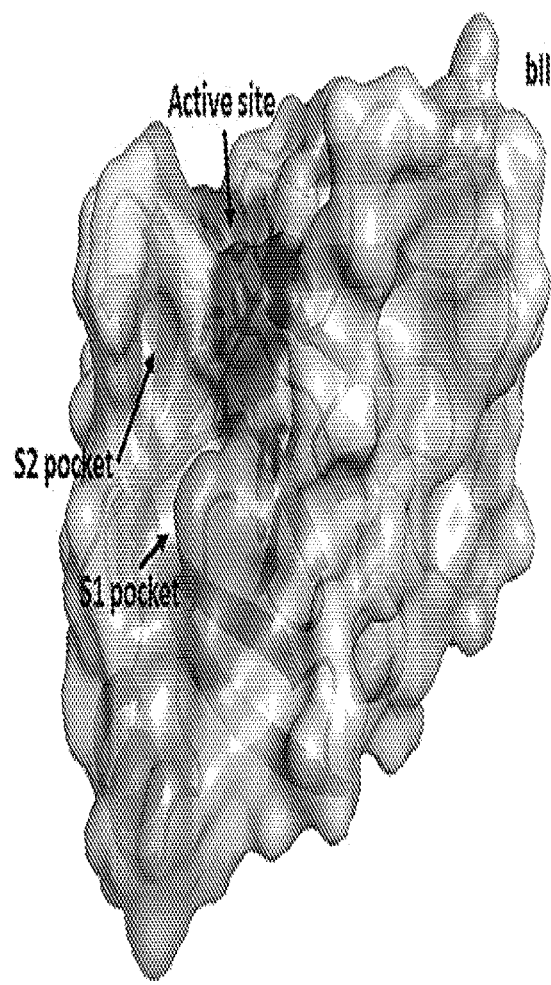
FIGS. 11A and 11B show structure of the HOV Pro. The surface and cartoon representation of the HOV Pro structure determined in the P212121 space group, with four molecules in the asymmetric unit. (11A) Surface representation of the HOV Pro monomer A with color-coded active site (magenta) and S1 (cyan) and S2 (yellow) substrate binding pockets. (11B) Cartoon representation of the monomer A. Catalytic residues H30, E54, and C139 (magenta), R112 and T185 are rendered as sticks, with nitrogen shown in blue and oxygen shown in red. Hydrogen bonds are indicated by black dashed lines. The flexible bII-cII loop and the S1 and S2 pockets are indicated with black arrows.

Overall structure of the HOV Pro. The HOV Pro crystals diffracted to 2.5 Å, and the structure was determined in the $P2_12_12_1$ space group with four molecules in the crystallographic asymmetric unit. The phases were resolved by MR using previously determined NV Pro structure as an initial model and refined with a final $R_{work}$ and $R_{free}$ values of 22.6% and 26.6%, respectively (FIG. 14). The overall structure is conserved and is comprised of a chymotrypsin-like fold with an N-terminal β-barrel and a C-terminal twisted β-sheet domains separated by a cleft where the active site is located, similar to other viral cysteine proteases (FIG. 11). All four monomers (A, B, C, and D) in the asymmetric unit were identical and superimposed with a root mean square deviation (RMSD) of ~0.79 Å. Molecules A and D, B and C form distinct tail-to-tail dimers in which the β-barrel of each HOV Pro monomer interacts along the crystallographic two-fold symmetry to form a dimer. The dimeric forms have been reported to be important for the functions of other viral cysteine proteases, such as hepatitis A virus 3C protease and the coronavirus 3C protease (Zeitler, et al., 2006; Anand, et al., 2003; Peters, et al., 2005).

Figure 12A:
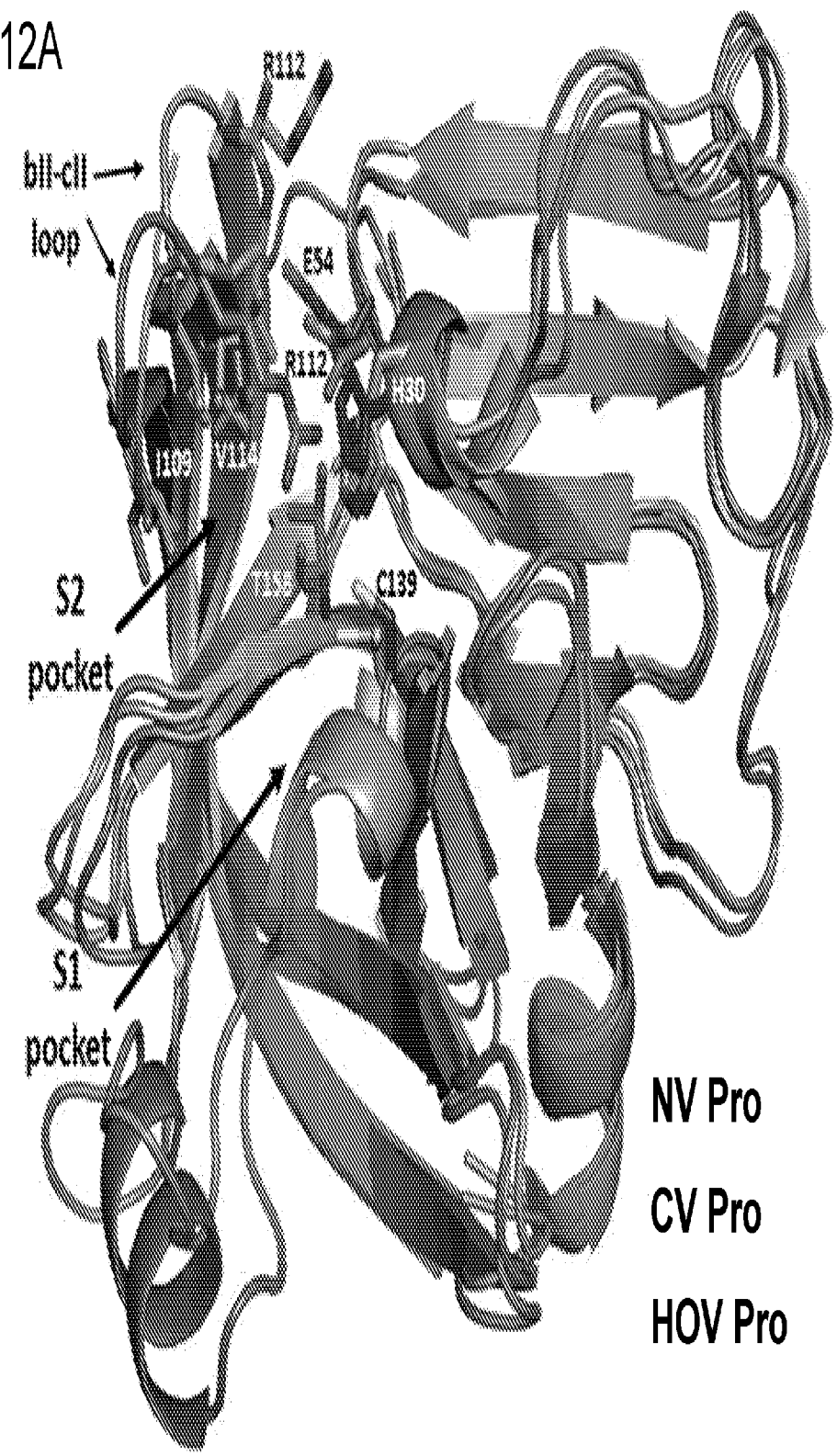

The substrate binding pockets. While the overall structure of the HOV Pro is similar to that of the NV Pro, substantial changes were observed, particularly in the S1 and S2 pockets that interact with the P1 and P2 residues of the substrate, respectively. In the HOV Pro structure, the S1 pocket is slightly shifted, compared to that in the GI protease structures (FIG. 12A). Although shifted, the superposition of the NV Pro structure in complex with substrates or inhibitors indicates that S1 pocket in the HOV Pro should be able to accommodate the P1 residue (Q or E) without any steric clashes. The residues 122-136 that form the floor of the S1 pocket exhibit more significant changes. In the HOV Pro this stretch consists of an α-helix, whereas in the GI protease structures it is generally unstructured. The S2 pocket, however, shows more significant differences. It is distinctly smaller than that in the NV Pro structure because of the conformational changes in the bII-cII loop with an RMSD of 4.56 Å for the matching Ca atoms between HOV and NV Pro structures. In this respect, the S2 pocket in HOV Pro more closely resembles that in the CV Pro structure in which the bII-cII loop is oriented in a similar manner and S2 pocket is also smaller compared to the NV Pro. As a result of this change, residues I109, R112, and V114 in the HOV Pro are positioned facing the active site pocket (FIG. 12B).

Figure 11B:
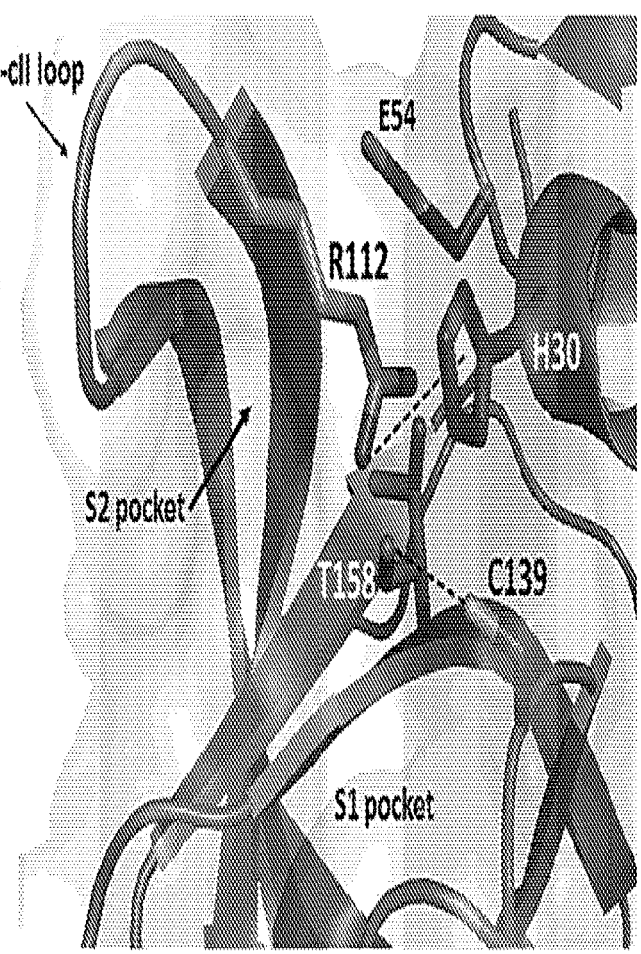

Catalytic triad or dyad? Further notable changes were observed in the catalytic triad residues of the HOV Pro (FIG. 11B). In the NV Pro, the triad residues form a network of hydrogen bonds with nucleophilic C139 interacting with basic H30 that functions to deprotonate and polarize C139, and H30, in turn, forming a hydrogen bond with the acidic E54 that serves to properly align the imidazole ring of H30 with respect to C139 (Zeitler, et al., 2006; Muhaxhiri, et al., 2013). Residues H30, C139, and E54 are conserved in all GI and GII.4 proteases. However, in the HOV Pro structure, all three residues show changes in their side chain orientations, compared to the NV Pro structure (FIGS. 11B and 12B). The side chain density for E54 in the HOV Pro structure is not well resolved indicating a high conformational flexibility of this residue. Strikingly, instead of H30 interacting with E54, as observed in other NoV Pro structures, H30 closely interacts with the side chain of R112. Modeling the E54 residue in the same orientation as observed in the NV Pro structure showed a steric clash with R112, indicating that the side chain of E54 has to be turned away from the active site to accommodate R112 side chain in the close proximity of H30. As a result of its interaction with R112, the orientation of the imidazole ring of H30 is also markedly different, from that observed in the previous NoV Pro structures. In that orientation, neither of the two nitrogen atoms of the imidazole is placed at a proper distance to effectively deprotonate the sulfhydryl (SH) group of C139 for the nucleophilic attack. The shortest distance between one of the imidazole nitrogen atoms and the SH of C139 is 3.9 Å, which is significantly longer than what is observed in other GI protease structures. The side chain of C139 is also oriented slightly differently compared to the NV Pro structure, with its SH group hydrogen bonded to main chain carbonyl atom of T158. Such a hydrogen bond interaction is not observed in other GI protease structures.

HOV Pro activity is pH-sensitive. The observations of the unusual configuration of the active site residues with a unique histidine-arginine pairing along with the consideration that the structure of the HOV Pro was determined at pH 6.5 lead the inventors to consider that R112 could influence the catalytic activity of HOV Pro in a pH-dependent manner. To directly test this consideration, the inventors used a FRET assay to measure the $k_{cat}/K_m$-enzyme efficiency of the both HOV and NV proteases at pHs 8, 6.5, and 5 using the decapeptide sequence containing P1-P5 and P1'-P5' that corresponds to cleavage site between p48-p41 in the their respective polyproteins. The FRET assay showed that while HOV Pro was active at pH 8, it showed no activity at pH 6.5 and pH 5 (FIG. 15). In contrast, NV Pro, in which R112 is positioned away from the active site because of the differential changes bII-cII loop, was optimally active at pH 8 and retained its activity albeit at a reduced level at pH 6.5 (FIG. 15), indicating that the presence of the arginine in the active site is likely the reason for the greater pH sensitivity of HOV Pro. To further test this the inventors made R112A mutant and performed similar activity assay. Unlike the wild-type HOV Pro, R112A mutant was active at pH 6.5.

The FRET assays at pH 8 further revealed that HOV Pro cleaves its substrate at a slower rate ($k_{cat}/K_m$=843.7 $M^{-1}s^{-1}$) than the NV Pro ($k_{cat}/K_m$=1423.2 $M^{-1}s^{-1}$) (FIG. 15). Mutating R112 to alanine in the HOV Pro resulted in a higher affinity for the substrate and higher cleavage efficiency of the HOV Pro R112A ($k_{cat}/K_m$=1215 $M^{-1}s^{-1}$), compared to the wild-type HOV Pro, suggesting that the R112 may regulate the rate of the catalysis by the protease by limiting the substrate access to the S2 pocket. Taken together, these results show that R112 plays an important role in substrate affinity/activity of the protease and this regulation may be pH-dependent.

Figure 13A:
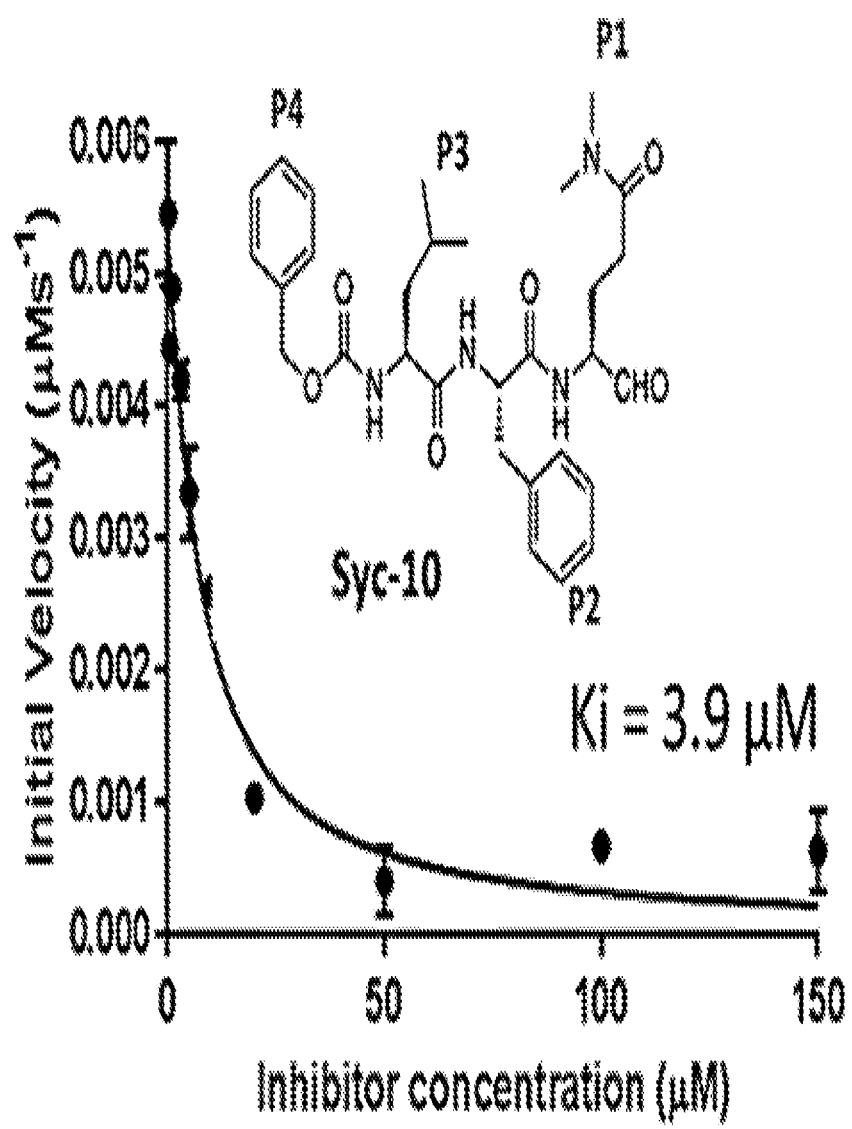
FIG. 13 provides rates of substrate hydrolysis by the HOV Pro R112A in the presence of the Syc-10 and Syc-59 aldehyde inhibitors. Substrate hydrolysis was measured by FRET, as described above, in the presence of the increasing concentrations of the Syc-10 and Syc-59 inhibitor. The $K_i$ values were determined by fitting the initial velocities to the Morrison tight-binding equation, using GraphPad Prism 7.
Figure 13B:
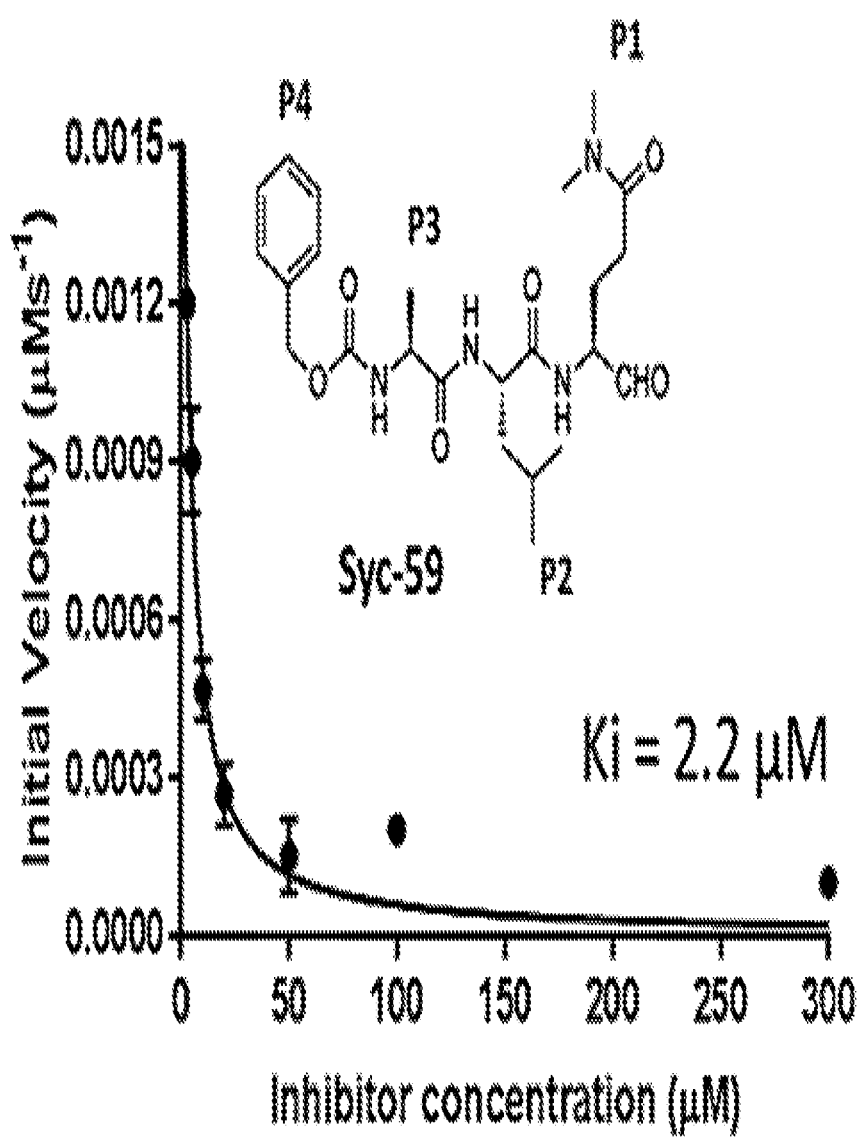

R112A mutant shows improved inhibitor potency compared to wild-type. Previously the inventors designed a panel of substrate-based inhibitors that mimic the P1-P4 substrate residues of the NV polyprotein with a terminal reactive group targeting the active site. Crystal structures of the NV Pro in complex with two of the most potent inhibitors in this panel Syc-10 and Syc-59, each with glutamine at the P1 position, and phenylalanine and leucine residues, respectively, at the P2 position, showed the P1 and P2 residues fitting firmly into the S1 and S2 pockets of the NV Pro and the reactive group forming a covalent adduct with C139 and preventing formation of the oxyanion hole in the active site, a necessary step for cleavage (Muhaxhiri, et al., 2013). When tested with the HOV Pro, both inhibitors showed significantly reduced potency, compared to the NV Pro (Deng, et al., 2013). For this example, the inventors tested Syc-10 and Syc-59 against the HOV Pro R112A mutant to examine the how the absence of arginine sidechain differentially affects inhibitor efficiency. Both inhibitors showed improved inhibition against the R112A mutant. For Syc-10, with a bulkier phenylalanine at the P2 position, $K_i$ for the mutant was 3.9 µM, compared to the 7.5 µM (Deng, et al., 2013) for the wild-type protease, and for Syc-59, with leucine at the P2 position, $K_i$ for the mutant was 2.2 µM, compared to the 4.6 µM for the wild-type (Deng, et al., 2013) (FIG. 13). This strongly suggests that in the absence of arginine sidechain, the inhibitors were relatively more efficient compared to the wildtype but still not as efficiently as the NV Pro. Taken together, these findings indicate that the presence of arginine in the active site, conformational alterations in the active site residues, and the conformation of the bII-cII loop which narrows the S2 pocket, differentially affect both the catalytic and inhibitor efficiencies compared to NV Pro, and these factors should be considered in designing GII.4 specific or broad-spectrum inhibitors.

Significance of Certain Embodiments

Virus-encoded proteases have emerged as new targets for antiviral treatments and disease prevention. Inhibitors targeting the viral protease have been used effectively to treat infections caused by HIV (Sanne, et al., 2003; Pulido, et al., 2008; Kempf, et al., 1998), hepatitis C (Pause, et al., 2003; Lamarre, et al., 2003; Reesink, et al., 2006; Sarrazin, et al., 2007; Lin, et al., 2009), herpesvirus (Shimba, et al., 2004; Anderson, et al., 2009), human rhinoviruses (Hayden, et al., 2003), and SARS coronaviruses (Anderson, et al., 2009; Fear, et al., 2007). Advances in high-throughput screening of chemical compound libraries together with structure-based drug design have aided the development of these protease inhibitors. Among human NoVs, although some progress has been made in developing inhibitors against the GI proteases, these inhibitors are not as effective against the other genogroups, particularly the prevalent GII genogroup. To develop an effective broadly cross-reactive NoVs protease inhibitor it is critical to understand the structural differences among the viral proteases of these two genogroups. To address this, the inventors determined the protease structure of a GII.4 NoV (HOV variant). Comparison of the structure with the GI protease structure shows that although the overall polypeptide fold is conserved among the NoV proteases, substantial structural changes were observed in the vicinity of the active site and these differences could differentially affect both catalytic and inhibitor efficacies.

HOV Pro structure shows significant differences compared to GI proteases. The overall structure of the HOV Pro resembles that of the GI protease structures as well as the other typical cysteine proteases. In contrast to the other NoV protease structures, the S2 substrate binding pockets of the HOV Pro is markedly smaller. The bII-cII loop of the S2 pocket is highly flexible (Nakamura, et al., 2005) and the S2 pocket of the NV Pro was shown to exist in three conformations: closed (unbound protease), semi-open (TALE-bound), and open (INFE-bound) (Muhaxhiri, et al., 2013). However, even in the closed conformation, the S2 pocket of the NV Pro is larger than the S2 pocket of the HOV Pro. The structure of GI.4 protease CV Pro also showed a smaller S2 pocket, compared to the NV Pro structure (Zeitler, et al., 2006). In that study, the authors modeled the substrate mimicking oligopeptide bound to the protease active site showing the P1 and P2 residues of the peptide fitting into the S1 and S2 pockets without any significant clashes. The authors concluded that the smaller S2 pocket would still be able to accommodate the large P2 residue of the natural substrate (Nakamura, et al., 2005). This suggests that the reduction of the inhibitor potency that was observed between the NV and the HOV Pro may not be solely attributed to the smaller S2 pocket. In some embodiments of the disclosure, changes in the substrate binding pockets in the HOV Pro structure together with the conformational changes of the catalytic residues, presence of R112 side chain in the active site plus the changes in some of the amino acids surrounding the active site, all contribute to the reduced inhibitor efficiencies against the HOV Pro, as discussed below.

HOV Pro active site presents a unique configuration of the catalytic residues. In addition to the changes in the S1 and S2 pockets, the HOV Pro structure showed significant changes in the active site where all three catalytic residues had different orientations, compared to the NV Pro. Unexpectedly, in the HOV Pro, the role of the E54 residue in stabilizing catalytic H30 appears to be taken up by R112. A somewhat similar observation was made in the enterovirus 71 3C protease (EV71 Pro) structure in which in addition to the catalytic C147, H40, and E71, two other residues, arginine (R39) and asparagine (N69), were shown to be important for catalysis. R39 and N69 formed hydrogen bonds with E71 connecting it via a hydrogen bond network to the H40 and C147 and providing the correct environment for the efficient cleavage. The mutation of these residues to the alanine resulted in an inactivated EV71 Pro (Wang, et al., 2011). In the HOV Pro the removal of the R112 side chain with an alanine mutation from the active site enhanced HOV Pro activity suggesting that, unlike any other 3C proteases, HOV Pro uses a novel catalytic site configuration that is sensitive to pH.

In another example, hepatitis A 3C protease lacks the third member of the catalytic triad only utilizing the cysteine (C172) and histidine (H44) to cleave. The structure of the hepatitis A protease revealed a water molecule occupying the position of the third member of the triad. An additional residue, tyrosine 143 (Y143), was also found in the active site but the distances between Y143 and H44 or Y143 and the water molecule were too great to make any hydrogen bonds (Bergmann, et al., 1997). The authors speculated that the role of the negatively charged Y143 was to stabilize electrostatically a positive charge of the H44 imidazole ring during the rate-limiting transition state, a role that could be played by R112 in the HOV Pro.

The rotamer analysis of R112 in the NV Pro structure using COOT showed that any of the possible side chain orientations cannot come close the to the active site side chain to make similar interaction with H30 as observed in the HOV Pro structure because of the rather extended conformation of the bII-cII loop. The same analysis of the R112 in the CV Pro structure, which has a similar conformation of the bII-cII loop as in HOV Pro structure, showed that alternate orientations of R112 side chain could engage in similar R112-H30 interactions as observed in the HOV Pro structure. On the other hand, alternate conformations of R112 sidechain in the HOV Pro would allow E54 to hydrogen bond with H30 and position it appropriately to interact with C139 required for protease activation. In some aspects, the role of the R112 in the HOV Pro may be to regulate protease activity by disrupting the canonical triad interactions.

Unusual Arg-His pairing confers pH sensitivity to HOV Pro. A unique feature of HOV Pro is the R112-H30 interaction. Although such a pairing between the two positively charged residues is uncommon, under certain conditions, they can participate in stabilizing interactions. Such interactions are contingent upon the protonation state of the histidine's imidazole ring, which is highly pH dependent (Browne, et al., 1976; Khandogin, et al., 2006; Miyagi, et al., 2008; Heyda, et al., 2010). The studies showed that HOV Pro becomes inactive at acidic pH 6.5 whereas the NV Pro still retains some of its activity at this pH. Such differential sensitivity to pH could be attributed to the presence of R112 in the catalytic pocket of HOV Pro and its close interaction with H30. At pH 6.5, the protonation state of the imidazole ring of H30 increases shifting the equilibrium more toward the aromatic ($\pi$-system) state and allowing it to participate in a stabilizing cation-$\pi$ interaction with R112 as observed in the structure, which as noted before was determined from crystals obtained at pH 6.5. At pH 8, however, the protonation state of the H30 decreases and the equilibrium shifts more toward the cationic state of the imidazole ring leading to destabilization of the H30-R112 interaction and allowing R112 sidechain to assume a different orientation. With the sidechain of R112 moved away, the side chain of E54 can then assume an orientation conducive for hydrogen bonding with the partially protonated state of H30 allowing it to be placed appropriately to abstract proton from the SH group of C139 for the nucleophilic attack when the substrate is bound. The pH sensitivity is not as pronounced in the GI protease, which is active at both neutral and pH 6.5. A plausible explanation is that in the absence of R112, even at this pH, some cationic nature of H30 is retained and E54 is able to hydrogen bond with H30 and position it appropriately toward the SH group of C139. Such a reasoning is consistent with the observation that removing R112 from the active site restored some of the HOV Pro activity at pH 6.5. Both the NV and the HOV Pro are completely inactive at pH<6.0. At such pH values, below the pKa of histidine, the imidazole ring is expected to be fully protonated and in such a state it will not be able to abstract the proton from SH group of C139 for the nucleophilic attack.

A structure of the HOV Pro in complex with its native substrate would shed a definitive light on the mechanism of substrate binding to the HOV Pro and the role R112 and the role pH may play in this binding. Regardless, the histidine-arginine pairing of the catalytic residues has not been observed in any other viral cysteine proteases and represents a significant example of the viral protease evolution also creating a unique challenge in developing the inhibitors potent against GII.4 viruses.

HOV Pro exhibits lower enzyme efficiency than NV Pro. The biochemical studies indicate that the HOV Pro has a lower affinity for its substrate and lower proteolytic efficiency, compared to the NV Pro. This surprising observation raises a set of interesting questions: is the presence of the arginine in the active site a rate limiting factor for proteolytic cleavage? Is it possible that in the infected cells virus uses pH to regulate proteolysis? Is the slower rate of proteolytic cleavage translates to the more efficient viral replication? A study by Belliot et al. showed that the NoV RNA-dependent RNA polymerase (RdRp) may exist in two forms during the NoV infection: Pol (the mature polymerase) and ProPol (a precursor comprised of both the protease and polymerase). ProPol still exhibited full protease activity and had consistently higher polymerase activity and for longer periods of time than Pol (Belliot, et al., 2005; Scheffler, et al., 2007), suggesting that the ProPol form of the polymerase would be preferred by the virus. The same observation was made for the ProPol protein of feline calicivirus (FCV), another member of the Caliciviridae, in which ProPol was a predominant form of the RdRp observed in FCV-infected cells (Sosnovtseva, et al., 1999; Wei, et al., 2001). Assuming that, like in the GI, both Pol and ProPol polymerase forms also exist in the GII.4 viruses, it is possible that the slower rate of polyprotein cleavage by the HOV Pro will result in the uncleaved or partially cleaved polyprotein components, among them ProPol, being present for longer periods of time, allowing the ProPol to replicate viral RNA more efficiently. Therefore a slower rate of polyprotein cleavage could potentially be advantageous for the GII.4 NoV.

Figure 16B:
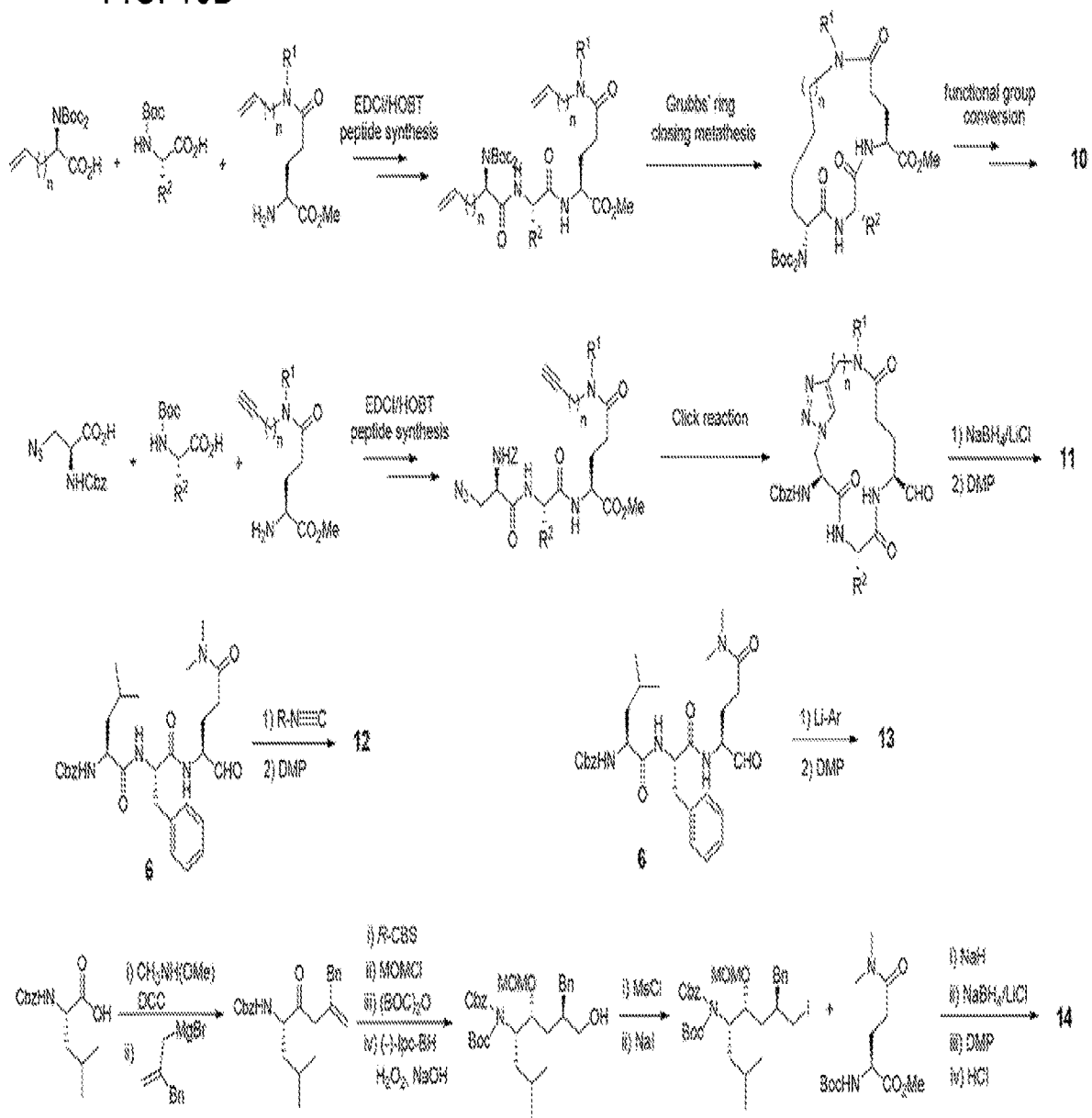
FIG. 16B illustrates examples of synthesis schemes for the inhibitors.

Changes in the HOV Pro active site reduce the potency of GI inhibitors. The inhibitors designed based on the GI structures were less inhibitory to the HOV Pro (Ng, et al., 2015). This indicates that the steric hindrance for the P2 residues of the inhibitor created by the changes in the HOV Pro S2 pocket and the active site play a significant role in lowering the inhibitor potency. Most likely the difference observed is due not to just one factor but to the combination of all of the differences found in the HOV Pro structure. However, mutation of R112 to the alanine improved inhibitor potency, indicating the importance of R112 plays in the inhibitor binding to the protease active site. Furthermore, the Syc-59 inhibitor that has a leucine residue in the P2 position was more potent against the wild-type HOV Pro and the R112 mutant, compared to the Syc-10 inhibitor that has a bulkier phenylalanine in the P2 position. Thus, a viable potential strategy for designing GII.4-specific inhibitors would be to design inhibitors with smaller P2 residues. Another strategy would be to design dipeptide inhibitors that will only include the reactive group and the P1 residue which would allow to avoid steric clashes in the S2 pocket altogether.

In summary, the studies in this example describe the first atomic structure of the GII.4 NoV protease HOV Pro. The structure reveals unique interactions between the catalytic residues of the HOV Pro not observed in the previously reported structures of the GI proteases. In particular embodiments, these unusual residue interactions are associated with the inhibitor potencies between the GI.1 and GII.4 proteases and may be considered when designing a broadly cross-reactive protease inhibitors.

Example 3

Design and Synthesis of Second-Generation Inhibitors of Noroviral Proteases

The present example concerns structure-based approaches as well as medicinal chemistry to design and develop potent and, at least in some cases, broadly active inhibitors of noroviral proteases (NVPro). Potent NVPro inhibitors with $K_i$ values as low as 75 nM have been identified, while these compounds exhibit weakened activity against HOVPro. In addition, these compounds all have an aldehyde functional group, which could be deactivated quickly in vivo. Moreover, as these antiviral compounds are expected to be working in the gastrointestinal tract, consideration of metabolic stability of these compounds is helpful. These points represent rationale for design and synthesis of second-generation inhibitors of noroviral proteases, guided by X-ray structures of NVPro:inhibitor complexes.

a) Inhibitor design. Using structure-based approaches and medicinal chemistry, the present example considers design and synthesis of novel compounds targeting noroviral proteases, as exemplified in FIG. 16A, in an effort to obtain potent and metabolically stable inhibitors with broad activity.

One strategy is to design and synthesize macrocyclic inhibitors. The structure of NVPro indicated that the P1 and P3 side chains of the inhibitor are in proximity (~6 Å). A macrocyclic compound linking the two moieties in at least some embodiments is useful to have improved inhibitory potency because of less entropy costs upon binding to the protein (the ring restricts free bond rotation). In addition, cyclic peptidic or peptidomimetic compounds possess considerably higher resistance to enzymatic hydrolysis, which could provide desired metabolic stability in the gastrointestinal tract. As an initial trial, compound 9 (FIG. 16A) with a 19-membered ring, which mimics a most potent inhibitor 7 (FIG. 16A) has been synthesized and found to be also a strong NVPro inhibitor with a $K_i$ value of 0.5 μM. Preliminary X-ray crystallography study showed while the P2, P1 and aldehyde have a similar binding mode, the linker ring between P1 and P3 is largely unordered. This suggests the ring size is bigger than perfection, which might be responsible for the weakened activity. In some embodiments, one can initially synthesize a series of cyclic peptidic compounds, such as compounds 10 and 11 with 15-18 membered rings (FIG. 16).

One strategy is to identify new electrophilic groups that can replace the aldehyde in current inhibitors. In previous SAR studies, analogs of 6 (SYC-10) with a terminal —COOH or α,β-unsaturated ester exhibited no activity against NVPro, while that with a methyl ketone (—COMe) showed >100-fold activity loss. These results indicate that a more reactive group may be useful. One can synthesize compounds 12 and 13 (FIG. 16), for example, bearing an activated ketone. The amide[6] or other electron-withdrawing aromatic groups in these compounds may enhance the activity of the ketone and provide an effective warhead for NoV protease inhibition.

To further strengthen the resistance to hydrolysis, analogous compounds without an amide bond can be synthesized, such as compound 14 (FIG. 16), where the 0 atom of the Y group and the P1 —NH— could still form two H-bonds with the enzyme. The rationale for this design is that since the NVPro:6 structure reveals that the P2 —NH— and —CO— do not form H-bonds with the enzyme, analogs without these two moieties (e.g., 14)(FIG. 16) could maintain a similar inhibitory activity, while these non-peptidic compounds are resistant to hydrolysis in the GI tract and are useful as drugs, in certain embodiments.

One can generate inhibitors with broad activity. Previous studies show compounds bearing a smaller P2 side chain is useful to inhibit HOVPro. One can synthesize several analogs of 6 with a smaller P2 side chain, i.e., H, Me, Et, i-Pr and $CH_2OH$. The activity of these compounds, in addition to previous inhibitors, can be tested against NVPro and HOVPro. These SAR studies can reveal the structural requirements for a broad inhibitor of noroviral proteases.

b) SAR analysis and next-cycle inhibitor design. One can perform structure activity relationship (SAR) analysis including quantitative SAR to correlate the activities of new compounds with their chemical structures, from which further inhibitor design and synthesis can be carried out in order to find compounds with improved potency.

c) Synthesis. FIG. 16B shows general methods for synthesizing exemplary compounds. The key macrocycle formation steps for making 9-11 are well established ring-closing-metathesis and click reactions. Alternative synthetic approaches may be used to obtain these compounds, as well.

Examples of specific inhibitors are included in FIGS. 17, 18, and 19.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

Adams P D, Grosse-Kunstleve R W, Hung L W, Ioerger T R, McCoy A J, Moriarty N W, Read R J, Sacchettini J C, Sauter N K, Terwilliger T C. 2002. PHENIX: building new software for automated crystallographic structure determination. Acta Crystallogr D Biol Crystallogr 58:1948-1954.

Ahmed S M, Hall A J, Robinson A E, Verhoef L, Premkumar P, Parashar U D, Koopmans M, Lopman B A. 2014. Global prevalence of norovirus in cases of gastroenteritis: a systematic review and meta-analysis. Lancet Infect Dis 14:725-730.

Anand K, Ziebuhr J, Wadhwani P, Mesters J R, Hilgenfeld R. 2003. Coronavirus main proteinase (3CLpro) structure: basis for design of anti-SARS drugs. Science 300:1763-1767.

Anderson J, Schiffer C, Lee S K, Swanstrom R. 2009. Viral protease inhibitors. Handb Exp Pharmacol doi:10.1007/978-3-540-79086-0_4:85-110.

Atmar R L, Estes M K. 2006. The epidemiologic and clinical importance of norovirus infection. Gastroenterol Clin North Am 35:275-290, viii.

Bazan J F, Fletterick R J. 1988. Viral cysteine proteases are homologous to the trypsin-like family of serine proteases: structural and functional implications. Proc Natl Acad Sci USA 85:7872-7876.

Belliot G, Sosnovtsev S V, Chang K O, Babu V, Uche U, Arnold J J, Cameron C E, Green K Y. 2005. Norovirus proteinase-polymerase and polymerase are both active forms of RNA-dependent RNA polymerase. J Virol 79:2393-2403.

Belliot G, Sosnovtsev S V, Mitra T, Hammer C, Garfield M, Green K Y. 2003. In vitro proteolytic processing of the MD145 norovirus ORF1 nonstructural polyprotein yields stable precursors and products similar to those detected in calicivirus-infected cells. J Virol 77:10957-10974.

Bergmann E M, Mosimann S C, Chernaia M M, Malcolm B A, James M N. 1997. The refined crystal structure of the 3C gene product from hepatitis A virus: specific proteinase activity and RNA recognition. J Virol 71:2436-2448.

Blakeney S J, Cahill A, Reilly P A. 2003. Processing of Norwalk virus nonstructural proteins by a 3C-like cysteine proteinase. Virology 308:216-224.

Boniotti B, Wirblich C, Sibilia M, Meyers G, Thiel H J, Rossi C. 1994. Identification and characterization of a 3C-like protease from rabbit hemorrhagic disease virus, a calicivirus. J Virol 68:6487-6495.

Browne C A, Campbell I D, Kiener P A, Phillips D C, Waley S G, Wilson I A. 1976. Studies of the histidine residues of triose phosphate isomerase by proton magnetic resonance and x-ray crystallography. J Mol Biol 100:319-343.

Collaborative Computational Project N. 1994. The CCP4 suite: programs for protein crystallography. Acta Crystallogr D Biol Crystallogr 50:760-763.

Damalanka V C, Kim Y, Galasiti Kankanamalage A C, Lushington G H, Mehzabeen N, Battaile K P, Lovell S, Chang K O, Groutas W C. 2017. Design, synthesis, and evaluation of a novel series of macrocyclic inhibitors of norovirus 3CL protease. Eur J Med Chem 127:41-61.

Deng L, Muhaxhiri Z, Estes M K, Palzkill T, Prasad B V, Song Y. 2013. Synthesis, Activity and Structure-Activity Relationship of Noroviral Protease Inhibitors. Medchemcomm 4.

Emsley P, Cowtan K. 2004. Coot: model-building tools for molecular graphics. Acta Crystallogr D Biol Crystallogr 60:2126-2132.

Fear G, Komarnytsky S, Raskin I. 2007. Protease inhibitors and their peptidomimetic derivatives as potential drugs. Pharmacol Ther 113:354-368.

Glass P J, White L J, Ball J M, Leparc-Goffart I, Hardy M E, Estes M K. 2000. Norwalk virus open reading frame 3 encodes a minor structural protein. J Virol 74:6581-6591.

Green K Y, Ando T, Balayan M S, Berke T, Clarke I N, Estes M K, Matson D O, Nakata S, Neill J D, Studdert M J, Thiel H J. 2000. Taxonomy of the caliciviruses. J Infect Dis 181 Suppl 2:S322-330.

Hardy M E, Crone T J, Brower J E, Ettayebi K. 2002. Substrate specificity of the Norwalk virus 3C-like proteinase. Virus Res 89:29-39.

Hardy M E, Estes M K. 1996. Completion of the Norwalk virus genome sequence. Virus Genes 12:287-290.

Hayden F G, Turner R B, Gwaltney J M, Chi-Burris K, Gersten M, Hsyu P, Patick A K, Smith G J, 3rd, Zalman L S. 2003. Phase I I, randomized, double-blind, placebo-controlled studies of ruprintrivir nasal spray 2-percent suspension for prevention and treatment of experimentally induced rhinovirus colds in healthy volunteers. Antimicrob Agents Chemother 47:3907-3916.

Heyda J, Mason P E, Jungwirth P. 2010. Attractive interactions between side chains of histidine-histidine and histidine-arginine-based cationic dipeptides in water. J Phys Chem B 114:8744-8749.

Jiang X, Wang M, Wang K, Estes M K. 1993. Sequence and genomic organization of Norwalk virus. Virology 195:51-61.

Kabsch W. 2010. Xds. Acta Crystallogr D Biol Crystallogr 66:125-132.

Kempf D J, Rode R A, Xu Y, Sun E, Heath-Chiozzi M E, Valdes J, Japour A J, Danner S, Boucher C, Molla A, Leonard J M. 1998. The duration of viral suppression during protease inhibitor therapy for HIV-1 infection is predicted by plasma HIV-1 RNA at the nadir. AIDS 12:F9-14.

Khandogin J, Chen J, Brooks C L, 3rd. 2006. Exploring atomistic details of pH-dependent peptide folding. Proc Natl Acad Sci USA 103:18546-18550.

Lamarre D, Anderson P C, Bailey M, Beaulieu P, Bolger G, Bonneau P, Bos M, Cameron D R, Cartier M, Cordingley M G, Faucher A M, Goudreau N, Kawai S H, Kukolj G, Lagace L, LaPlante S R, Narj es H, Poupart M A, Rancourt J, Sentj ens R E, St George R, Simoneau B, Steinmann G, Thibeault D, Tsantrizos Y S, Weldon S M, Yong C L, Llinas-Brunet M. 2003. An NS3 protease inhibitor with antiviral effects in humans infected with hepatitis C virus. Nature 426:186-189.

Lin T I, Lenz O, Fanning G, Verbinnen T, Delouvroy F, Scholliers A, Vermeiren K, Rosenquist A, Edlund M, Samuelsson B, Vrang L, de Kock H, Wigerinck P, Raboisson P, Simmen K. 2009. In vitro activity and preclinical profile of TMC435350, a potent hepatitis C virus protease inhibitor. Antimicrob Agents Chemother 53:1377-1385.

Lindesmith L C, Donaldson E F, Baric R S. 2011. Norovirus GII.4 strain antigenic variation. J Virol 85:231-242.

Matthews D A, Smith W W, Ferre R A, Condon B, Budahazi G, Sisson W, Villafranca J E, Janson C A, McElroy H E, Gribskov C L, et al. 1994. Structure of human rhinovirus 3C protease reveals a trypsin-like polypeptide fold, RNA-binding site, and means for cleaving precursor polyprotein. Cell 77:761-771.

McCoy A J, Grosse-Kunstleve R W, Adams P D, Winn M D, Storoni L C, Read R J. 2007. Phaser crystallographic software. J Appl Crystallogr 40:658-674.

Miyagi M, Nakazawa T. 2008. Determination of pKa values of individual histidine residues in proteins using mass spectrometry. Anal Chem 80:6481-6487.

Mosimann S C, Cherney M M, Sia S, Plotch S, James M N. 1997. Refined X-ray crystallographic structure of the poliovirus 3C gene product. J Mol Biol 273:1032-1047.

Muhaxhiri Z, Deng L, Shanker S, Sankaran B, Estes M K, Palzkill T, Song Y, Prasad B V. 2013. Structural basis of substrate specificity and protease inhibition in Norwalk virus. J Virol 87:4281-4292.

Nakamura K, Someya Y, Kumasaka T, Ueno G, Yamamoto M, Sato T, Takeda N, Miyamura T, Tanaka N. 2005. A norovirus protease structure provides insights into active and substrate binding site integrity. J Virol 79:13685-13693.

Ng T F, Zhang W, Sachsenroder J, Kondov N O, da Costa A C, Vega E, Holtz L R, Wu G, Wang D, Stine C O, Antonio M, Mulvaney U S, Muench M O, Deng X, Ambert-Balay K, Pothier P, Vinje J, Delwart E. 2015. A diverse group of small circular ssDNA viral genomes in human and non-human primate stools. Virus Evol 1:vev017.

Pause A, Kukolj G, Bailey M, Brault M, Do F, Halmos T, Lagace L, Maurice R, Marquis M, McKercher G, Pellerin C, Pilote L, Thibeault D, Lamarre D. 2003. An NS3 serine protease inhibitor abrogates replication of subgenomic hepatitis C virus RNA. J Biol Chem 278:20374-20380.

Peters H, Kusov Y Y, Meyer S, Benie A J, Bauml E, Wolff M, Rademacher C, Peters T, Gauss-Muller V. 2005. Hepatitis A virus proteinase 3C binding to viral RNA: correlation with substrate binding and enzyme dimerization. Biochem J 385:363-370.

Pulido F, Arribas J R, Delgado R, Cabrero E, Gonzalez-Garcia J, Perez-Elias M J, Arranz A, Portilla J, Pasquau J, Iribarren J A, Rubio R, Norton M, Group OKS. 2008. Lopinavir-ritonavir monotherapy versus lopinavir-ritonavir and two nucleosides for maintenance therapy of HIV. AIDS 22:F1-9.

Ramani S, Atmar R L, Estes M K. 2014. Epidemiology of human noroviruses and updates on vaccine development. Curr Opin Gastroenterol 30:25-33.

Reesink H W, Zeuzem S, Weegink C J, Forestier N, van Vliet A, van de Wetering de Rooij J, McNair L, Purdy S, Kauffman R, Alam J, Jansen P L. 2006. Rapid decline of viral RNA in hepatitis C patients treated with VX-950: a phase Ib, placebo-controlled, randomized study. Gastroenterology 131:997-1002.

Sanne I, Piliero P, Squires K, Thiry A, Schnittman S, Group AICT. 2003. Results of a phase 2 clinical trial at 48 weeks (AI424-007): a dose-ranging, safety, and efficacy comparative trial of atazanavir at three doses in combination with didanosine and stavudine in antiretroviral-naive subjects. J Acquir Immune Defic Syndr 32:18-29.

Sarrazin C, Rouzier R, Wagner F, Forestier N, Larrey D, Gupta S K, Hussain M, Shah A, Cutler D, Zhang J, Zeuzem S. 2007. SCH 503034, a novel hepatitis C virus protease inhibitor, plus pegylated interferon alpha-2b for genotype 1 nonresponders. Gastroenterology 132:1270-1278.

Scheffler U, Rudolph W, Gebhardt J, Rohayem J. 2007. Differential cleavage of the norovirus polyprotein precursor by two active forms of the viral protease. J Gen Virol 88:2013-2018.

Shimba N, Nomura A M, Marnett A B, Craik C S. 2004. Herpesvirus protease inhibition by dimer disruption. J Virol 78:6657-6665.

Someya Y, Takeda N, Miyamura T. 2002. Identification of active-site amino acid residues in the Chiba virus 3C-like protease. J Virol 76:5949-5958.

Someya Y, Takeda N, Miyamura T. 2005. Characterization of the norovirus 3C-like protease. Virus Res 110:91-97.

Sosnovtsev S V, Garfield M, Green K Y. 2002. Processing map and essential cleavage sites of the nonstructural polyprotein encoded by ORF1 of the feline calicivirus genome. J Virol 76:7060-7072.

Sosnovtseva S A, Sosnovtsev S V, Green K Y. 1999. Mapping of the feline calicivirus proteinase responsible for autocatalytic processing of the nonstructural polyprotein and identification of a stable proteinase-polymerase precursor protein. J Virol 73:6626-6633.

Vinje J. 2015. Advances in laboratory methods for detection and typing of norovirus. J Clin Microbiol 53:373-381.

Vongpunsawad S, Venkataram Prasad B V, Estes M K. 2013. Norwalk Virus Minor Capsid Protein VP2 Associates within the VP1 Shell Domain. J Virol 87:4818-4825.

Wang J, Fan T, Yao X, Wu Z, Guo L, Lei X, Wang J, Wang M, Jin Q, Cui S. 2011. Crystal structures of enterovirus 71 3C protease complexed with rupintrivir reveal the roles of catalytically important residues. J Virol 85:10021-10030.

Wei L, Huhn J S, Mory A, Pathak H B, Sosnovtsev S V, Green K Y, Cameron C E. 2001. Proteinase-polymerase precursor as the active form of feline calicivirus RNA-dependent RNA polymerase. J Virol 75:1211-1219.

Zeitler C E, Estes M K, Venkataram Prasad B V. 2006. X-ray crystallographic structure of the Norwalk virus protease at 1.5-A resolution. J Virol 80:5050-5058.

---

What is claimed is:

1. A composition of matter, comprising compound 1076 (Formula V)

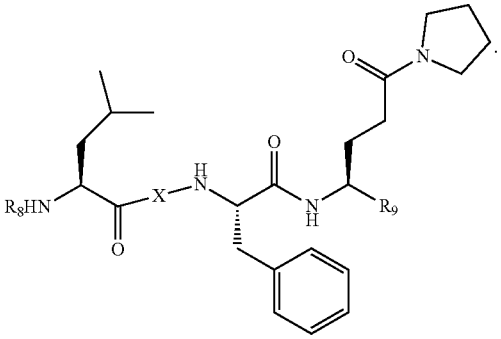

2. A pharmaceutical composition, comprising the composition of claim 1.

3. The pharmaceutical composition of claim 2, wherein the composition is formulated in a cream, solution, pill, tablet, suppository, film, or enema.

4. A cleaning composition, comprising the composition of claim 1.

5. The composition of claim 4, wherein the composition is a solution or cream.

6. The composition of claim 4, wherein the composition is in and/or on a substrate.

7. The composition of claim 6, wherein the substrate is selected from the group consisting of a towel, a wipe, and a sponge.

* * * * *